(12) United States Patent
Cleek et al.

(10) Patent No.: US 8,496,953 B2
(45) Date of Patent: *Jul. 30, 2013

(54) IMMOBILIZED BIOLOGICALLY ACTIVE ENTITIES HAVING A HIGH DEGREE OF BIOLOGICAL ACTIVITY FOLLOWING STERILIZATION

(75) Inventors: Robert L. Cleek, Flagstaff, AZ (US); Michael D. Daly, Flagstaff, AZ (US); Krzysztof R. Pietrzak, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 960 days.

This patent is subject to a terminal disclaimer.

(21) Appl. No.: 11/433,105

(22) Filed: May 12, 2006

(65) Prior Publication Data

US 2007/0264301 A1 Nov. 15, 2007

(51) Int. Cl.
*A61F 2/00* (2006.01)

(52) U.S. Cl.
USPC ........................................................... 424/423

(58) Field of Classification Search
None
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 4,326,532 A | 4/1982 | Hammer |
| 4,329,383 A | 5/1982 | Joh |
| 4,415,490 A | 11/1983 | Joh |
| 4,526,714 A | 7/1985 | Feijen et al. |
| 4,600,652 A | 7/1986 | Solomon et al. |
| 4,613,665 A | 9/1986 | Larm |
| 4,678,671 A | 7/1987 | Feijen et al. |
| 4,745,180 A | 5/1988 | Moreland et al. |
| 4,810,784 A | 3/1989 | Larm |
| 4,944,767 A | 7/1990 | Barbucci et al. |
| 5,032,666 A | 7/1991 | Hu et al. |
| 5,130,143 A * | 7/1992 | Strickland et al. ......... 424/94.64 |
| 5,213,898 A | 5/1993 | Larm et al. |
| 5,308,617 A | 5/1994 | Halluin |
| 5,417,969 A * | 5/1995 | Hsu et al. ...................... 424/423 |
| 5,476,666 A | 12/1995 | Rhee et al. |
| 5,510,418 A | 4/1996 | Rhee et al. |
| 5,527,524 A | 6/1996 | Tomalia et al. |
| 5,529,986 A * | 6/1996 | Larsson et al. .................. 514/54 |
| 5,532,311 A * | 7/1996 | Sirvio et al. .................. 525/54.2 |
| 5,583,213 A | 12/1996 | Yafuso et al. |
| 5,876,433 A * | 3/1999 | Lunn ............................ 623/1.15 |
| 5,897,955 A | 4/1999 | Drumheller |
| 5,914,182 A | 6/1999 | Drumheller |
| 5,916,585 A | 6/1999 | Cook et al. |
| 5,922,690 A | 7/1999 | Van Gorp et al. |
| 6,120,536 A | 9/2000 | Ding et al. |
| 6,406,687 B1 | 6/2002 | Luthra et al. |
| 6,440,947 B1 | 8/2002 | Barron et al. |
| 6,461,665 B1 | 10/2002 | Scholander |
| 6,642,242 B2 | 11/2003 | Collis et al. |
| 6,787,179 B2 | 9/2004 | Timm et al. |
| 6,887,249 B1 | 5/2005 | Houser et al. |
| 7,045,585 B2 | 5/2006 | Berry et al. |
| 7,641,682 B2 | 1/2010 | Palmaz et al. |
| 7,662,409 B2 * | 2/2010 | Masters ........................ 424/484 |
| 7,736,687 B2 | 6/2010 | Sims et al. |
| 2001/0036932 A1 | 11/2001 | Cardin et al. |
| 2001/0044654 A1 * | 11/2001 | Chen et al. .................... 623/1.41 |
| 2002/0146414 A1 | 10/2002 | Sakiyama-Elbert |
| 2003/0135195 A1 | 7/2003 | Jimenez et al. |
| 2003/0161938 A1 * | 8/2003 | Johnson ...................... 427/2.28 |
| 2004/0254419 A1 * | 12/2004 | Wang et al. ........................ 600/8 |
| 2005/0025797 A1 * | 2/2005 | Wang et al. .................... 424/422 |
| 2005/0059068 A1 | 3/2005 | Huang et al. |
| 2005/0079132 A1 * | 4/2005 | Wang et al. .................. 424/1.11 |
| 2005/0079200 A1 * | 4/2005 | Rathenow et al. ............ 424/423 |
| 2005/0220839 A1 | 10/2005 | DeWitt et al. |
| 2005/0232971 A1 * | 10/2005 | Hossainy et al. ............. 424/426 |
| 2006/0204533 A1 | 9/2006 | Hsu et al. |
| 2007/0010702 A1 * | 1/2007 | Wang et al. ........................ 600/8 |
| 2007/0098708 A1 | 5/2007 | Myette |
| 2007/0212388 A1 | 9/2007 | Patravale |
| 2007/0264302 A1 | 11/2007 | Cleek et al. |
| 2007/0264308 A1 | 11/2007 | Cleek et al. |
| 2008/0267903 A1 | 10/2008 | Uchegbu et al. |
| 2008/0279909 A1 * | 11/2008 | Cleek et al. .................. 424/423 |
| 2009/0274737 A1 | 11/2009 | Borck |

FOREIGN PATENT DOCUMENTS

| | | |
|---|---|---|
| EP | 0086186 | 2/1983 |
| EP | 0086187 | 2/1983 |
| EP | 0495820 | 7/1992 |
| EP | 0923953 | 6/1999 |
| EP | 0 956 870 | 11/1999 |
| EP | 1559434 | 8/2005 |
| EP | 1559434 A1 * | 8/2005 |
| EP | 1916260 | 4/2008 |

(Continued)

OTHER PUBLICATIONS

Hardhammer et al. "Reduction in Thrombotic Events With Heparin-Coated Palmaz-Schatz Stents in Normal Porcine Coronary Arteries" Circulation (1996); 93; 423-430.*

(Continued)

*Primary Examiner* — Robert A Wax
*Assistant Examiner* — Olga V Tcherkasskaya

(57) ABSTRACT

The present invention is directed to immobilized biologically active entities that retain significant biological activity following sterilization of the immobilized biologically active entities.

54 Claims, 12 Drawing Sheets

FOREIGN PATENT DOCUMENTS

| WO | 87/07156 | 12/1987 |
|---|---|---|
| WO | 93/05793 | 4/1993 |
| WO | 97/07834 | 3/1997 |
| WO | 98/08552 | 3/1998 |
| WO | WO 9808552 A1 * | 3/1998 |
| WO | 00/01843 | 1/2000 |
| WO | 01/41827 | 6/2001 |
| WO | 01/87375 | 11/2001 |
| WO | 03/057270 | 7/2003 |
| WO | 2005/018552 | 3/2005 |
| WO | 2007/133699 | 11/2007 |
| WO | 2008/063157 | 5/2008 |
| WO | 2010/029189 | 3/2010 |

OTHER PUBLICATIONS

Peter A. Hårdhammar, Heleen M.M. van Beusekom, Håkan U. Emanuelsson, Sjoerd H. Hofma, Per A. Albertsson, Pieter D. Verdouw, Eric Boersma, Patrick W. Serruys, Willem J. van der Giessen. Reduction in Thrombotic Events With Heparin-Coated Palmaz-Schatz Stents in Normal Porcine Coronary Arteries1 . 1996, Circulation 93:423-430.*

Lin PH, Chronos NA, Marijianowski MM, Chen C, Bush RL, Conklin B, Lumsden AB, Hanson SR. Heparin-coated balloon-expandable stent reduces intimal hyperplasia in the iliac artery in baboons. J Vasc Interv Radiol. May 2003;14(5):603-11.*

Gavalas VG, Chaniotakis NA, Gibson TD. Improved operational stability of biosensors based on enzyme-polyelectrolyte complex adsorbed into a porous carbon electrode. Biosensors & Bioelectronics 1998;13;1205-1211.

Gibson TD, Pierce BLJ, Parker SM. Stabilisation of the Biological component of Biosensors. Biosensors for Food Analysis 1998; 46-53.

Rocchietti S, Ublali D, Terreni M, et al. Immobilization and Stabilization of Recombinant Mulitmeric Uridine and Purine Nucleoside Phosphorylases from *Bacillus subtilis*. Biomacromolecules 2004; 5:2195-2200.

Hardhammar, PA, van Beusekom HMM, Emanuelsson HU, et al. Reduction in Thrombotic Events With Heparin-Coated Palmaz-Schatz Stents in Normal Procine Coronary Arteries. Circulation 1996; v93 n2:423-430.

Lin PH, Chronos NA, Marijianowski MM, Chen C, et al. Heparin-coated Balloon-expandable Stent Reduces Intimal Hyperplasia in the Iliac Artery in Baboons. J Vasc Intery Radiol 2003; 14:603-611.

Choay J. Biologic studies on chemically synthesized pentasaccharide and tetrasaccharide fragments. Seminars in Thrombosis and Hemostasis 1985; 11:81-85.

Freudenberg U, Hermann A, Welzel P et al. A star-PEG-heparin hydrogel platform to aid cell replacement therapies for neurodegenerative diseases. Biomaterials 2009; 30: 5049-5060.

Griffith M. Heparin-catalyzed inhibitor/protease reactions: Kinetic evidence for a common mechanism of action of heparin. Proc. Natl. Acad. Sci. 1983; 80:5460-5464.

Horner A. Molecular-size-dependent variations in the proportions of chains with high binding affinities for antithrombin in rat skin heparin proteoglycans. Biochem. J. 1989; 262:953-958.

Kadir,A. Saccharide sensing using gold and silver nanoparticles—A review. Journal of Fluorescence. 2004;14:391-400.

Klement P, Du Y, Berry L et al. Blood-compatible biomaterials by surface coating with a novel antithrombin-heparin covalent complex. Biomaterials 2002; 23:527-535.

Lam L, Silbert J, Rosenberg R. The separation of active and inactive forms of heparin. Biochem. Biophys. Res. Comm. 1976; 69:570-577.

Larsen, M.L. et al., Assay of Plasma Heparin Using Thrombin and the Chromogenic Substrate H-D-Phe-Pip-Arg-pNA (S-2238). Thromb Res 1978; 13:285-288.

MacIntosh F. A colorimetric method for the standardization of heparin preparations. Biochem. 1941; 35:776-782.

Mulloy B, Forster, M. Conformation and dynamics of heparin and heparan sulfate. Glycobiology 2000; 10:1147-1156.

Oliveira G, Carvalho L, Silva M. Properties of carbodiimide treated heparin. Biomaterials 2003; 24: 4777-4783.

Pasche B, Elgue G, Olsson P et al. Binding of antithrombin to immobilized heparin under varying flow conditions. Artif. Organs 1991;15:481-491.

Rosenberg R, Jordan R, Favreau L et al. Highly active heparin species with multiple binding sites for antithrombin. Biochem. Biophys. Res. Comm. 1979; 86:1319-1324.

Tanzi M. Bioactive technologies for hemocompatibility. Expert Rev. Med. Devices 2005; 2:473-492.

Yamaguchi N, Kiick K. Polysaccharide-poly(ethylene glycol) star copolymer as a scaffold for the production of bioactive hydrogels. Biomacromolecules 2005; 6:1921-1930.

Linhardt RJ, Turnbull JE, Wang HM, Loganathan D, Gallagher T. (1990) Examination of the Substrate Specificity of Heparin and Heparan Sulfate Lyases. Biochemistry, vol. 29, p. 2611-2617.

Hinrichs WLJ, ten Hoopen HWM, Wissink MJB, Engbers GHM, Feijen J. (1997) Design of a new type of coating for the controlled release of heparin. Journal of Controlled Release, vol. 45, p. 163-176.

"Heparin", Wikipedia.com, 2012.

Lin PH, Chronos NA, Marijianowski MM, Chen C, Bush RL, Conklin B, Lumsden AB, Hanson SR. Heparin-coated Balloon-expandable Stent Reduces Intimal Hyperplasia in the Iliac Artery in Baboons. Journal of Vascular and Interventional Radiology 2003; vol. 14, No. 5, p. 603-611.

Lin PH, Chen C, Bush RL, Yao Q, Lumsden AB, Hanson SR. Small-caliber heparin-coated ePTFE grafts reduce platelet deposition and neointimal hyperplasia in a baboon model. Journal of Vascular Surgery 2004; vol. 39, No. 6, p. 1322-1328.

Lin PH, Bush RL, Yao Q, Lumsden AB, Chen C. Evaluation of Platelet Deposition and Neointimal Hyperplasia of Heparin-Coated Small-Caliber ePTFE Grafts in a Canine Femoral Artery Bypass Model. Journal of Surgical Research 2004; vol. 118, No. 1, p. 45-52.

Letourneur D, Machy D, Pellé A, Marcon-Bachari E, D'Angelo G, Vogel M, Chaubet F, Michel JB. Heparin and non-heparin-like dextrans differentially modulate endothelial cell proliferation: In vitro evaluation with soluble and crosslinked polysaccharide matrices. Journal of Biomedical Materials Research 2002; vol. 60, No. 1, p. 94-100.

Park KD, Kim YS, Han DK, Kim YH, Lee EHB, Suh H, Choi KS. Bacterial adhesion on PEG modified polyurethane surfaces. Biomaterials 1998; vol. 19, No. 7-9, p. 851-859.

Salu KJ, Bosmans JM, Bult H, Vrints CJ. Drug-eluting stents: a new treatment in the prevention of restenosis Part I: experimental studies. Acta Cardiologica 2004; vol. 59, No. 1, p. 51-61.

Leclerc G. Drug Delivery from PC-Coated Stents. Japanese Journal of Interventional Cardiology 2001; vol. 16, No. Suppl. 1, p. 107.

Hellstrom WJG, Hyun JS, Human L, Sanabria JA, Bivalacqua TJ, Leungwattanakij S. Antimicrobial activity of antibiotic-soaked, Resist™-coated Bioflex®. International Journal of Impotence Research 2003; vol. 15, No. 1, p. 18-21.

* cited by examiner

IMMOBILIZED BIOLOGICALLY ACTIVE ENTITIES HAVING A HIGH DEGREE OF BIOLOGICAL ACTIVITY FOLLOWING STERILIZATION

FIELD OF THE INVENTION

The present invention is directed to substrate materials having immobilized biologically active entities that maintain their biological activity following exposure to conditions of elevated heat, high humidity, antibiotic agents, and/or mechanical stress. The present invention is particularly useful in the field of medical devices.

BACKGROUND OF THE INVENTION

In the field of medical devices, glass, polymeric, and/or metallic materials are common substrate materials. These materials can be used for diagnostic devices or extracorporeal devices. With the exception of glass, many of the materials can be used for implantable devices.

Immobilization of biologically active entities on substrate materials in a biologically active form involves an appreciation of the respective chemistries of the entity and the substrate material. Modification of the chemical composition of a substrate material is often required to immobilize a biologically active entity thereon. This is usually accomplished by treating surfaces of the substrate material to generate a population of chemically reactive elements or groups, followed by immobilization of the biologically active entity with an appropriate protocol. With other substrate materials, surfaces of a substrate material are covered, or coated, with a material having reactive chemical groups incorporated therein. Biologically active entities are then immobilized on the substrate material through the reactive chemical groups of the covering material. A variety of schemes for covering, or coating, substrate materials have been described. Representative examples of biologically active entities immobilized to a substrate material with a covering, or coating, material are described in U.S. Pat. Nos.: 4,810,784; 5,213,898; 5,897,955; 5,914,182; 5,916,585; and 6,461,665.

When biologically active compounds, compositions, or entities are immobilized, the biological activity of these "biologics" can be negatively impacted by the process of immobilization. The biological activity of many of biologics is dependent on the conformation (i.e., primary, secondary, tertiary, etc.) of the biologic in its immobilized state. In addition to a carefully selected immobilization process, chemical alterations to the biologic may be required for the biologic to be incorporated into the covering material with a conformation that renders the biologic sufficiently active to perform its intended function.

Despite an optimized covering and immobilization scheme, additional processing, such as sterilization, can degrade the biological activity of the immobilized biologic. For implantable medical devices, sterilization is required prior to use. Sterilization may also be required for in vitro diagnostic devices having sensitivity to contaminants. Sterilization of such devices usually requires exposure of the devices to elevated temperature, pressure, and humidity, often for several cycles. In some instances, antibiotic agents, such as ethylene oxide gas (ETO) or vapor hydrogen peroxide are included in the sterilization process. In addition to sterilization, packaging or long-term storage of an immobilized biologic can degrade the activity of the biologic.

There exists a need for medical devices having biologically active entities immobilized thereon that can be subjected to sterilization, packaging, and/or storage without significant loss of biological activity. Such a medical device would have biologically compatible compositions or compounds included with the immobilized biological entities that serve to minimize degradation of the biological activity of the entities during sterilization, packaging, and/or storage. In some instances, the additional biologically compatible compositions or compounds would increase the biological activity of some biologically active entities following a sterilization procedure.

SUMMARY OF THE INVENTION

The present invention is directed to medical devices having substrate materials with biologically active entities immobilized thereon in combination with additional biologically compatible organic chemical compositions that enable the biologically active entities to retain significant biological activity following exposure of the immobilized entities to processing and storage conditions that would otherwise degrade the biological activity of the entities.

A suitable substrate material can be any material with a surface having reactive chemical groups that are capable of attaching, confining, or otherwise immobilizing a biologically active entity in a biologically active form to one or more surfaces of the substrate material. Substrate materials can also have a multiplicity of reactive chemical groups added to surfaces of the materials through the application of one or more covering compositions, or materials, to the surfaces. At least a portion of a covering material has chemical elements, groups, compounds, or components that are reactive to biologically active entities and serve to attach, confine, or otherwise immobilize a biologically active entity in a biologically active form to the covering material.

At least one type of biologically active entity is chemically attached, confined, or otherwise immobilized to suitable reactive chemical groups on the substrate material and/or covering material. Following immobilization of a plurality of biologically active entities to at least a portion of a multiplicity of reactive chemical groups present on a substrate material and/ or covering material, an additional biologically compatible organic composition is non-valently combined with the biologically active entities, substrate, and/or polymeric covering material. The biologically compatible organic composition interacts with the biologically active entities and reactive chemical groups of the substrate material and/or covering material to prevent the biologically active entities from loosing biological activity under conditions that would otherwise significantly degrade the biological activity of the entities. These conditions include sterilization and storage. With expandable endoluminal medical devices, for example, mechanical compaction and expansion of such devices during packaging and deployment can also significantly degrade the biological activity of the entities.

The additional biologically compatible organic composition seems to maintain the biological activity of the entities during sterilization, storage, and/or mechanical manipulation by limiting undesirable alterations to the entities often induced by sterilization, storage, and/or a mechanical manipulation process. The activity-diminishing alterations could include conformational changes to a biologically active entity obscuring an active site on the entity. The activity-diminishing alterations could also include interactions between neighboring biologically active entities. Rearrangements of biologically active entities with respect to a polymeric covering material are other possible activity-diminishing alterations to the entities. Simple denaturation, or other degradation, of the biologically active entities could be another means by which the entities loose biological activity. As described in greater detail herein, immobilized biologically active entities sterilized, stored, and/or mechanically manipulated in the presence of the additional biologically compatible organic composition retain a degree of biological activity significantly greater than a similar immobilized biologically active entity processed under the same conditions in the absence of the additional biologically compatible organic composition.

The additional biologically compatible organic composition can be removed from a sterilized medical device during post-sterilization processing or the composition can be removed by physiological processes of an implant recipient following deployment of the sterilized medical device at an implantation site.

Preferred biologically active entities reduce or inhibit thrombus formation on surfaces of a substrate and/or covering material. Glycosaminoglycans are preferred anti-thrombotic agents for use in the present invention, with heparin, heparin analogs, and derivatives being particularly preferred. Other preferred biologically active substances reduce undesirable cellular growth from tissue in which the present invention is implanted. Preferred anti-proliferative agents for use in the present invention include dexamethasone, rapamycin, and paclitaxel.

Accordingly, one embodiment of the present invention is a sterilized medical device comprising a substrate material, a polymeric covering material attached to at least a portion of a surface of said substrate material, a plurality of biologically active entities having anti-thrombin III binding activity covalently attached to at least a portion of said polymeric covering material, and a biologically compatible organic composition non-covalently combined with said polymeric covering material and said biologically active entities, wherein said biologically active entities have an anti-thrombin III binding activity of at least 5 picomoles anti-thrombin III per square centimeter (pmol/cm$^2$) substrate material following sterilization of said biologically active entities. In other embodiments, the anti-thrombin binding activity is at least 6 picomoles anti-thrombin III per square centimeter (pmol/cm$^2$) substrate material, at least 7 picomoles anti-thrombin III per square centimeter (pmol/cm$^2$) substrate material, at least 8 picomoles anti-thrombin III per square centimeter (pmol/cm$^2$) substrate material, at least 9 picomoles anti-thrombin III per square centimeter (pmol/cm$^2$) substrate material, or at least 10 picomoles anti-thrombin III per square centimeter (pmol/cm$^2$) substrate material. In some embodiments, the anti-thrombin III binding activity is at least 100 pmol/cm$^2$ picomoles anti-thrombin III per square centimeter (pmol/cm$^2$) substrate material.

In another embodiment, the invention is a sterilized medical device comprising a substrate material, a polymeric covering material attached to at least a portion of a surface of said substrate material, a first plurality of heparin molecules having anti-thrombin III binding activity end point attached to at least a portion of said polymeric covering material, and a biologically compatible organic composition non-covalently combined with said polymeric covering material and said first plurality of heparin molecules, wherein said first plurality of heparin molecules have an anti-thrombin III binding activity of at least 10 picomoles anti-thrombin III per square centimeter (pmol/cm$^2$) substrate material following sterilization of said first plurality of heparin molecules.

In another embodiment, the present invention is a sterilized medical device comprising a polymeric substrate material, a polymeric covering material attached to at least a portion of a surface of said substrate material, a first plurality of heparin molecules having anti-thrombin III binding activity end point attached to at least a portion of said polymeric covering material, and a composition comprising a second plurality of heparin molecules non-covalently combined with said polymeric covering material, wherein said first plurality of heparin molecules have an anti-thrombin III binding activity of at least 10 picomoles anti-thrombin III per square centimeter (pmol/cm$^2$) substrate material following sterilization of said first plurality of heparin molecules.

In yet another embodiment, the present invention is a sterilized medical device comprising a polymeric substrate material, a polymeric covering material attached to at least a portion of a surface of said substrate material, a first plurality of heparin molecules having anti-thrombin III binding activity end point attached to at least a portion of said polymeric covering material, and a composition comprising a second plurality of heparin molecules non-covalently combined with said polymeric covering material, wherein said first plurality of heparin molecules have an anti-thrombin III binding activity of at least 100 picomoles anti-thrombin III per square centimeter (pmol/cm$^2$) substrate material following sterilization of said first plurality of heparin molecules.

In each of these embodiments, at least a portion of the non-covalently combined biologically compatible organic composition or the second plurality of heparin molecules is released from the sterilized or mechanically manipulated medical device within several hours when placed in a 0.15M phosphate buffer solution having a temperature of about thirty-seven degrees centigrade and a substantially neutral pH. Presence of the released compounds can be detected in the buffer solution with routine assay techniques.

DETAILED DESCRIPTION OF THE INVENTION

The present invention is directed to materials and devices having biologically active entities immobilized thereto that retain significant biological activity following sterilization, packaging, and/or storage conditions that would otherwise significantly decrease the biological activity of the entities. The biological activity of an immobilized biological entity subjected to such conditions is positively influenced by the presence of at least one additional biologically compatible composition non-covalently combined with the biologically active entities. In most embodiments, the additional composition is an organic compound. In some embodiments, however, the biologically compatible composition is an inorganic compound. In preferred embodiments, the additional composition is a carbohydrate in the form of a polysaccharide. Preferred polysaccharides are glycosaminoglycans. Preferred glycosaminoglycans are heparin compositions, heparin analogs, and heparin derivatives.

Figure 1:
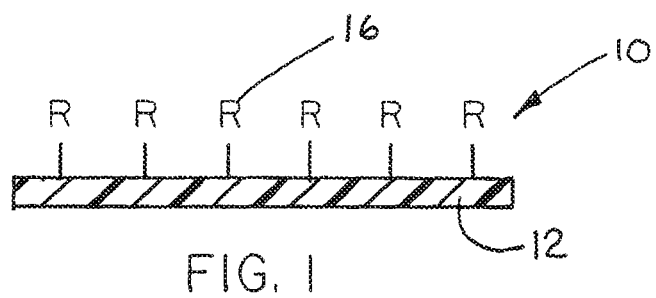
FIG. 1 is a schematic representation of a polymeric substrate material having a multiplicity of reactive chemical groups thereon.
Figure 2:
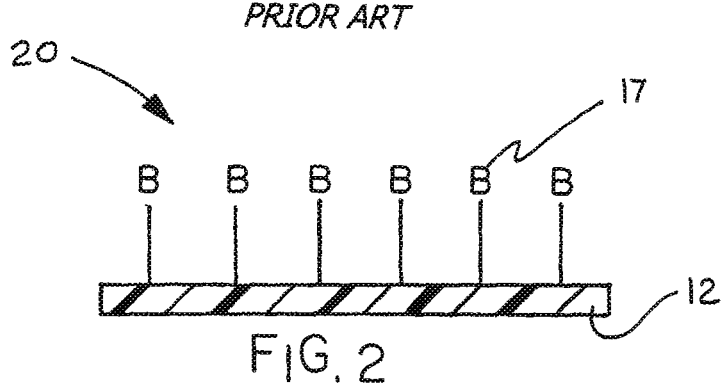
FIG. 2 is a schematic representation of a polymeric substrate material having a plurality of biologically active entities immobilized thereto.

Referring to FIGS. 1 and 2, some polymeric substrate materials (12) have multiplicities of reactive chemical groups (16) populating at least a portion of the surfaces of the substrate materials to which a plurality of biologically active entities (17) are attached, confined, or otherwise immobilized. Most biologically active entities (17) are covalently attached, or bound, to the substrate materials (12) through the reactive chemical groups (16). Surfaces of the polymeric substrate material (12) can be smooth, rough, porous, curved, planar, angular, irregular, or combinations thereof. In some embodiments, substrate materials with surface pores have internal void spaces extending from the porous surface of the material into the body of the material. These porous substrate materials have internal substrate material bounding the pores that often provides surfaces amenable to immobilizing biologically active entities. Whether porous or non-porous, substrate materials can be in the form of filaments, films, sheets, tubes, meshworks, wovens, non-wovens, and combinations thereof.

Suitable substrate materials (12) for immobilizing biologically active entities (17) include biocompatible polymeric materials such as polyethylene, polyurethane, silicone, polyamide-containing polymers, and polypropylene. Full density or porous polytetrafluoroethylene is a suitable polymeric substrate material (12) if reactive chemical groups (16) are introduced in constituents of the polymeric material. Substrate materials with a multiplicity of reactive chemical groups that are part of the substrate material are referred to herein as "functionalizable materials." Following reaction of a biologically active entity with a functionalizable substrate material, the substrate material is considered functionalized and the biologically active entity immobilized. In order to maintain the biological activity of the immobilized entity during subsequent processing conditions, such as sterilization, packaging, or storage, an additional biologically compatible organic chemical composition is non-covalently combined with the functionalized material and immobilized entity.

Substrate materials can also have a multiplicity of reactive chemical groups added to surfaces of the materials through the application of one or more covering compositions, or materials, to the surfaces. At least a portion of a covering material has chemical elements, groups, compounds, or components that are reactive to biologically active entities and serve to attach, confine, or otherwise immobilize a biologically active entity in a biologically active form to the covering material. The covering material can be applied in the form of a solute, particle, dispersion, coating, or overlay and attached to the substrate material in a variety of ways including, but not limited to, covalent bonding, adsorption, such as, physisorption or chemisorption, and non-covalent bonding, such as hydrogen bonding or ionic bonding. In preferred embodiments, the covering material is applied in a solution and forms a continuous or discontinuous film layer on one or more surfaces of the substrate material upon removal of the solvent. The covering material can be applied in one or more layers. The chemical constituents of the covering material in each layer can be the same or different. In some embodiments, the covering material is cross-linked to itself or other covering materials in other layers. The cross-linking bonds can be covalent or ionic.

Figure 1A:
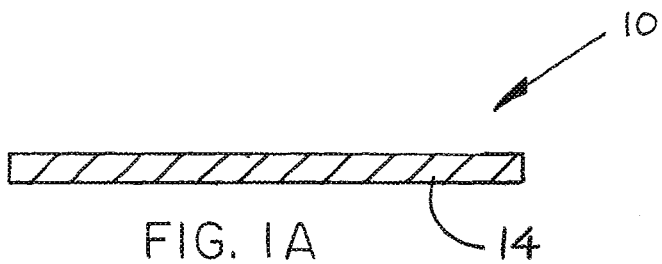
FIG. 1A is a schematic representation of a metallic substrate material.
Figure 3:
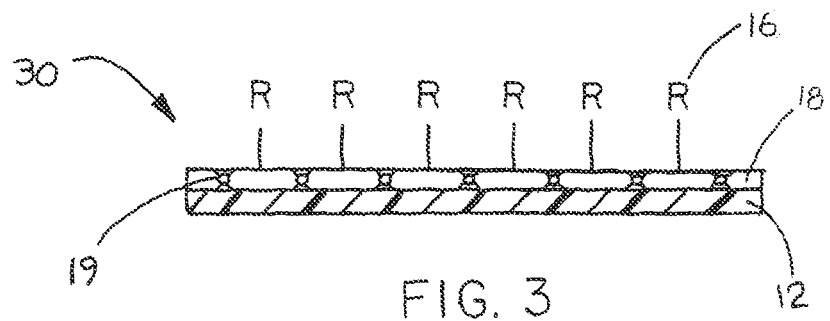
FIG. 3 is a schematic representation of a polymeric substrate material having a polymeric covering material with a multiplicity of reactive chemical groups thereon.
Figure 3A:
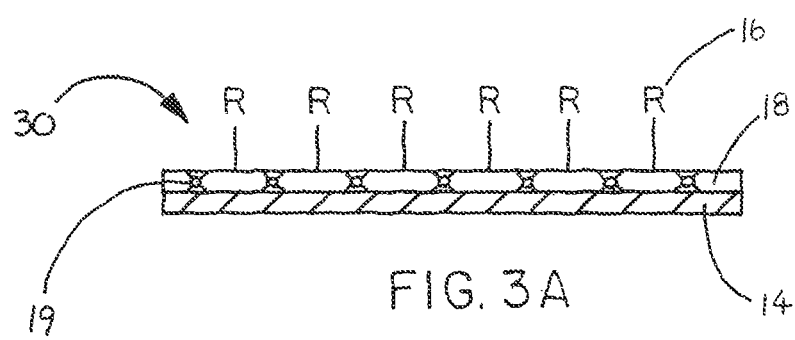
FIG. 3A is a schematic representation of a-metallic substrate material having a polymeric covering material with a multiplicity of reactive chemical groups thereon.
Figure 4:
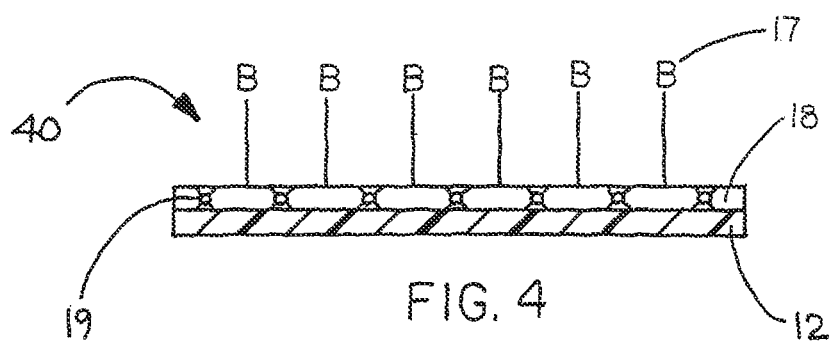
FIG. 4 is a schematic representation of a polymeric substrate material having a polymeric covering material with a plurality of biologically active entities immobilized thereto.
Figure 4A:
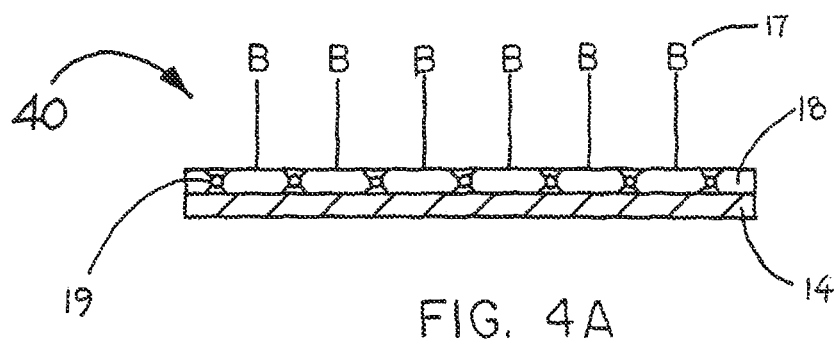
FIG. 4A is a schematic representation of a metallic substrate material having a polymeric covering material with a plurality of biologically active entities immobilized thereto.
Figure 7:
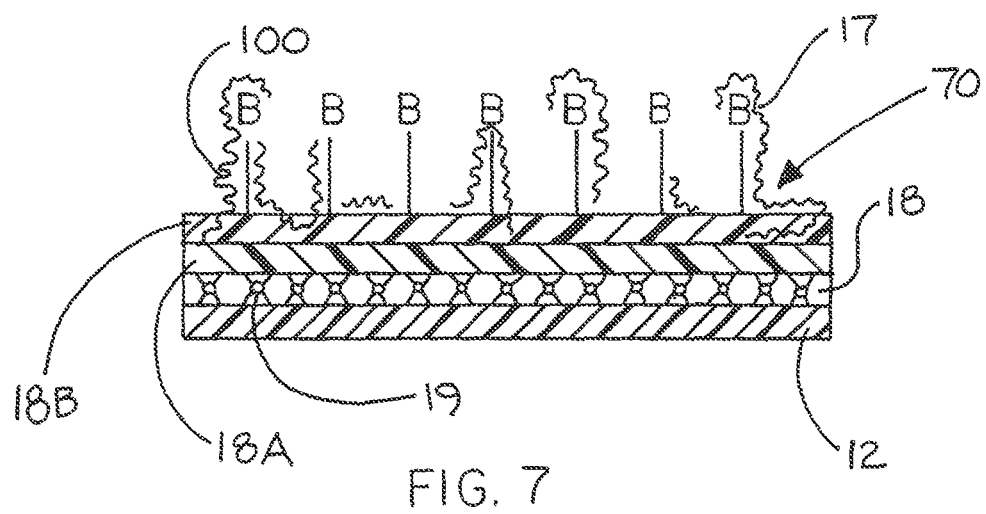
FIG. 7 is a schematic representation of a polymeric substrate material having three layers of polymeric covering material applied thereto with a plurality of biologically active entities immobilized thereto and an additional biologically compatible composition combined therewith.
Figure 7A:
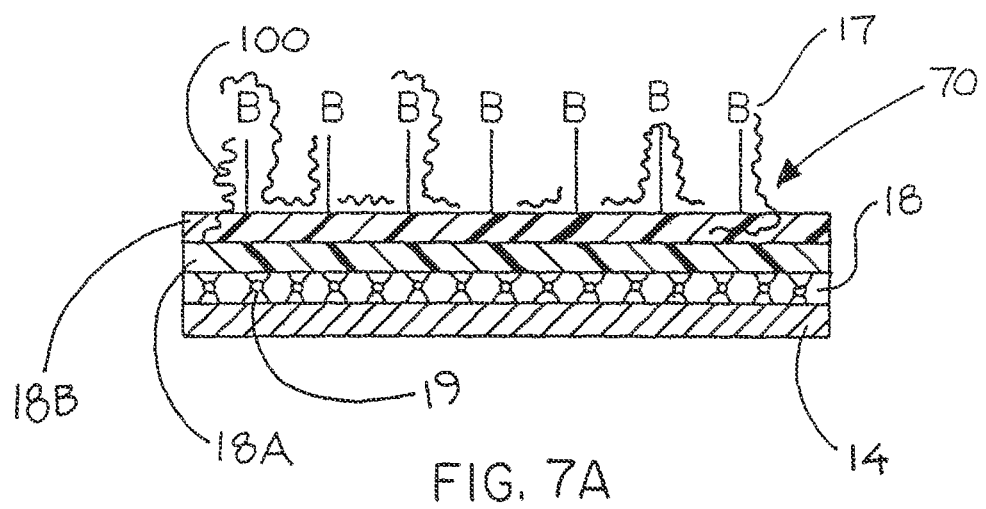
FIG. 7A is a schematic representation of a metallic substrate material having three layers of polymeric covering material applied thereto with a plurality of biologically active entities immobilized thereto and an additional biologically compatible composition combined therewith.
Figure 7B:
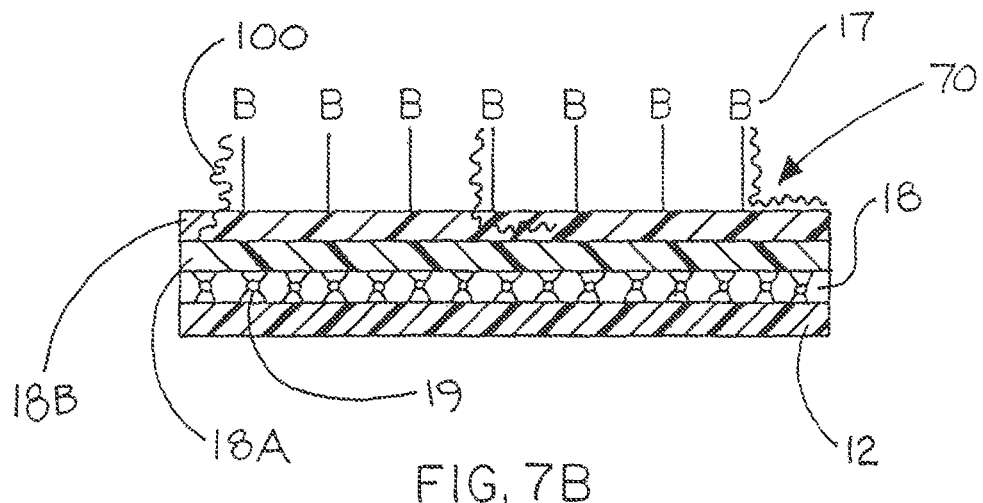
FIG. 7B is a schematic representation of a polymeric substrate material having three layers of polymeric covering material applied thereto with a plurality of biologically active entities immobilized thereto showing some of the biologically compatible composition illustrated in FIG. 7 having been released from the substrate material and polymeric covering material.
Figure 7C:
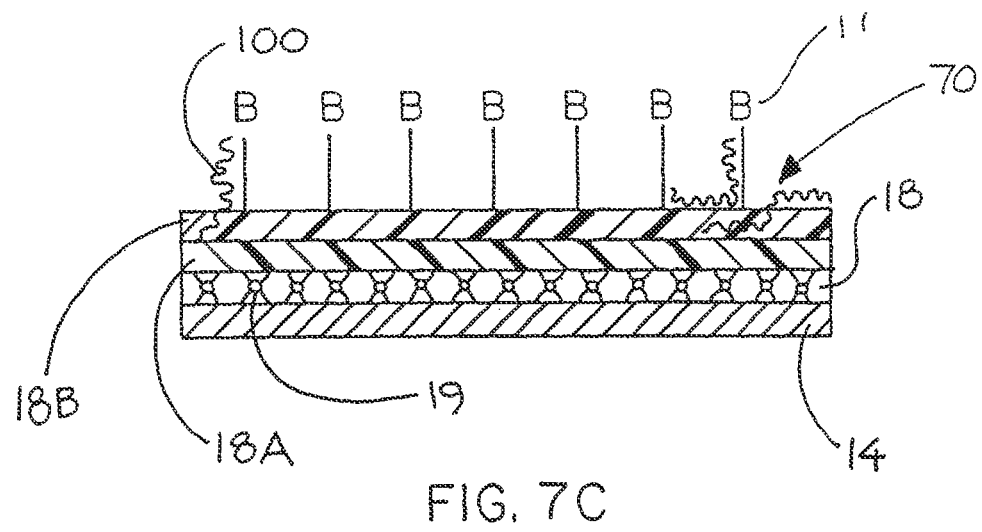
FIG. 7C is a schematic representation of a metallic substrate material having three layers of polymeric covering material applied thereto with a plurality of biologically active entities immobilized thereto showing some of the biologically compatible composition illustrated in FIG. 7A having been released from the substrate material and polymeric covering material.

Substrate materials (12, 14) lacking reactive chemical groups on their surfaces (FIG. 1A) (or lacking appropriately reactive chemical groups) are covered, at least in part, with a polymeric covering material (18) having a multiplicity of reactive chemical groups (16) thereon (FIGS. 3 and 3A) to which biologically active entities (17) can be attached, confined, or otherwise immobilized (FIGS. 4 and 4A). Most biologically active entities (17) are covalently attached, or bound, to the polymeric covering material (18) through the reactive chemical groups (16) of the covering material (18). The polymeric covering material (18) forms at least one layer on at least a portion of a substrate material (12, 14). In some embodiments, the polymeric covering material (18) is cross-linked (19) to itself or other layers (18a, 18b) of polymeric covering material (FIG. 7 and 7a). The cross-linking can be covalent, ionic, or both. Substrate materials amenable to covering are glass, metals (14), ceramics, polymeric materials (12), particularly chemically inert polymeric materials such as polytetrafluoroethylene.

At least one type of biologically active entity (17) is chemically attached, confined, or otherwise immobilized to suitable reactive chemical groups (16) on the substrate material (12, 14) and/or covering material (18). Biologically active entities (17) include, but are not limited to, antithrombotics, anticoagulants, fibrinolytic or thrombolytic agents, antibiotics, antiproliferatives, and anti-inflammatories. Antithrombotics of particular interest are glycosaminoglycans, particularly heparin, including derivatives and analogs thereof. Other anticoagulant agents include, but are not limited to, hiruidin, activated protein C, and prostaglandins. Fibrinolytic or thrombolytic agents include, but are not limited to, streptokinase, urokinase, and tissue plasminogen activatore (tPA). Other biologically active entities include, but are not limited to, enzymes, organic catalysts, ribozymes, organometallics, proteins, glycoproteins, peptides, polyamino acids, antibodies, nucleosides, nucleotides, nucleic acids, steroidal molecules, antibiotics, antimycotics, cytokines, carbohydrates, oleophobics, lipids, pharmaceuticals, and therapeutics.

While a variety of biologically active entities (17) can be used in the present invention, as described above, entities capable of interacting with components of mammalian blood to prevent coagulation or thrombus formation on surfaces of a substrate material (12, 14) or covering material (18) by the blood components are most preferred. Many of these biologically active entities are oligosaccharides or polysaccharides. Some of the polysaccharides are glycosaminoglycans including glucosamine or galactosamine compositions. Preferred glycosaminoglycans are heparin compositions, heparin analogs, and heparin derivatives. Heparin is a complex glycosaminoglycan with many biological functions mediated by its binding to growth factors, enzymes, morphogens, cell adhesions molecules, and cytokines. The biological activity of heparin to function as an anticoagulant is based on the ability of heparin to act as a catalyst for thrombin and antithrombin III (AT III) binding. Most of the anti-coagulant activity of heparin is associated with a pentasaccharide sequence that facilitates this binding.

The most preferred heparin composition for immobilization in the present invention is a heparin composition having a free terminal aldehyde group made according the teachings of U.S. Pat. No. 4,613,665, issued to Larm, which is incorporated herein by reference. In the process of making heparin with a free terminal aldehyde group, the heparin is subjected to degradation by diazotation to form a heparin fragment having a free terminal aldehyde group. The free terminal aldehyde group allows the heparin composition to be "end point attached" to primary amino groups of a substrate or polymeric covering material to form an imine which, by reduction, is converted to a secondary amine. End point attachment of the heparin composition permits the heparin to be immobilized in a conformation that most advantageously exposes the biologically active portion of the heparin composition to components of the blood responsible for coagulation and thrombus formation. When exposed to the blood components responsible for thrombus formation and coagulation, the optimally immobilized heparin interacts with the blood components to reduce or prevent thrombus formation or other coagulation events on surfaces of the substrate and/or covering material.

Other desirable biologically active entities (17) for use in the present invention include synthetic heparin compositions referred to as "fondaparinux," compositions involving antithrombin III-mediated inhibition of factor Xa, antiproliferatives, and anti-inflammatories.

Despite an optimized immobilization scheme, the biological activity of a heparin-based biological entity is significantly decreased during sterilization, packaging, and/or storage of the entities (FIGS. 9, 11, 12, and 13). As discussed above, the decrease in biological activity of an immobilized biologically active entity may be caused by a variety of factors. Regardless of the mechanism by which the biological activity of an immobilized entity is decreased, addition of a biologically compatible organic composition non-covalently combined with the immobilized biologically active entity maintains the biological activity of the entity during and after sterilization, packaging, and/or storage of the entities.

The additional biologically compatible organic composition can have biological activity or no biological activity. The additional biologically compatible organic composition can be a carbohydrate in the form of polyhydroxy aldehydes or ketones and their derivatives. These carbohydrates include monosaccharides, disaccharides, oligosaccharides, and polysaccharides, including glycosaminoglycans, glycosaminomannans, and storage polysaccharides such as dextran and its derivatives. Other biologically compatible organic compositions suitable for use in the present invention include acid mucopolysaccharides, amino acids, polypeptides, proteins, glycoproteins, nucleosides, nucdeotides, polynucleotides, or other biologically compatible aliphatic or aromatic compound, charged or uncharged, having a molecular weight less than about 100,000 MW.

Figure 5:
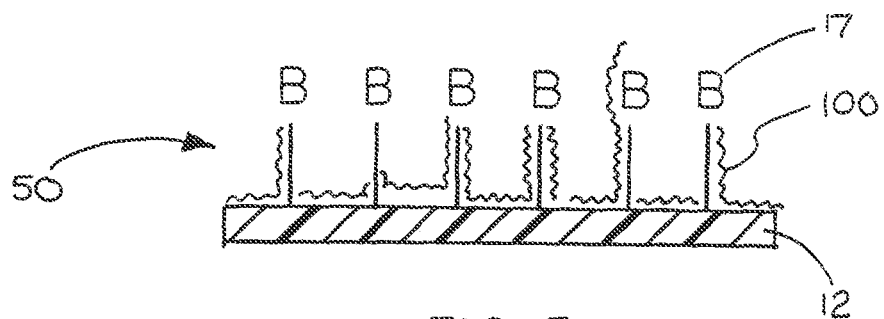
FIG. 5 is a schematic representation of a polymeric substrate material having a plurality of biologically active entities immobilized thereto and an additional biologically compatible composition combined therewith.
Figure 6:
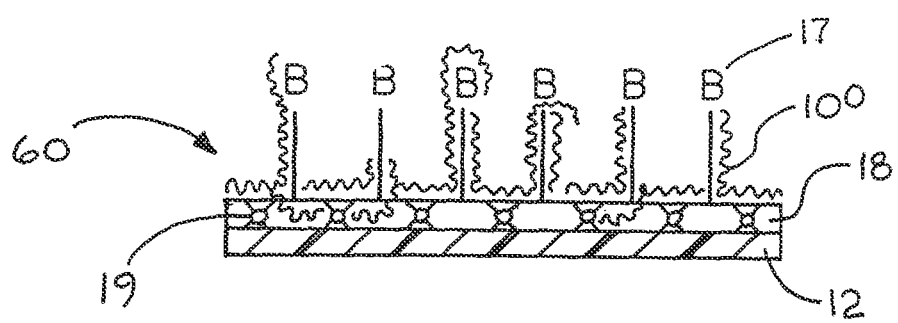
FIG. 6 is a schematic representation of a polymeric substrate material having a polymeric covering material with a plurality of biologically active entities immobilized thereto and an additional biologically compatible composition combined therewith.
Figure 6A:
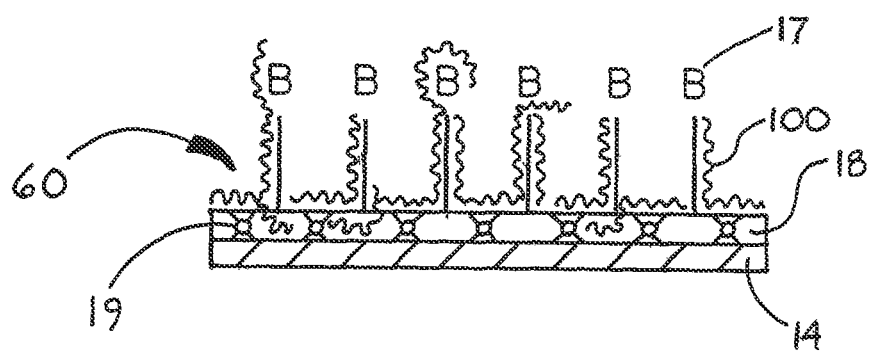
FIG. 6A is a schematic representation of a metallic substrate material having a polymeric covering material with a plurality of biologically active entities immobilized thereto and an additional biologically compatible composition combined therewith.
Figure 6B:
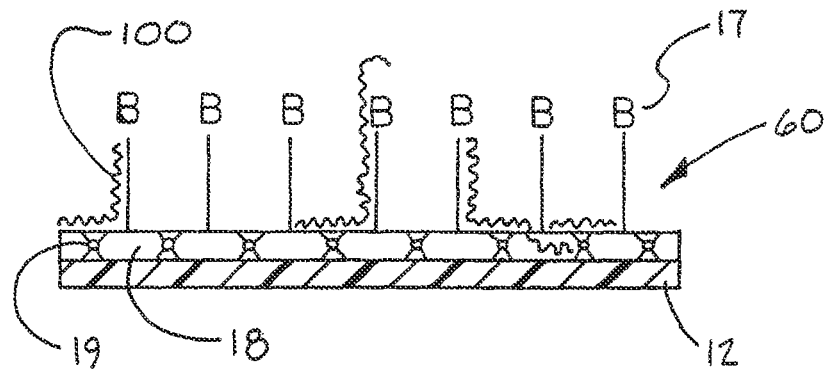
FIG. 6B is a schematic representation of a polymeric substrate material having a polymeric covering material with a plurality of biologically active entities immobilized thereto showing some of the biologically compatible composition illustrated in FIG. 6 having been released from the substrate material and polymeric covering material.
Figure 6C:
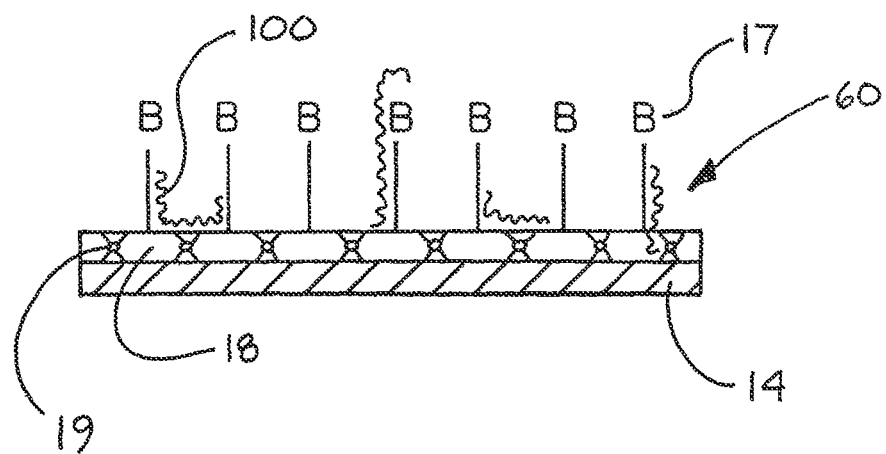
FIG. 6C is a schematic representation of a metallic substrate material having a polymeric covering material with a plurality of biologically active entities immobilized thereto showing some of the biologically compatible composition illustrated in FIG. 6A having been released from the substrate material and polymeric covering material.

Referring to FIGS. 5-6A, covered or uncovered substrate materials (14, 12, respectively) having biologically active entities (17) immobilized thereon have an additional biologically compatible composition (100) combined with the biologically active entities (17), the substrate material (12, 14) and/or the covering material (18). The biologically compatible composition is preferably organic. The biologically compatible organic composition can be applied to the immobilized biologically active entities, substrate, and/or covering material in a variety of ways. In a preferred embodiment, a suitable carbohydrate-based biologically compatible composition is dissolved in an aqueous solvent and the solution applied to the immobilized biologically active entities, substrate, and/or polymeric covering material by spraying, dip coating, immersing, rolling, spreading, or other deposition means. In appropriate systems, biologically compatible compositions can be dissolved in organic solvents and similarly applied.

The preferred embodiment of the present invention is a sterilized medical device for implantation, or other placement, at an anatomical site. Most preferred are sterilized medical devices for placement inside an anatomical structure delimiting a void space, or lumen, to reinforce the anatomical structure or maintain the void space delimited thereby. When these sterilized devices are used within a vascular structure, immobilized biologically active entities in the form of end point attached heparin interact with blood flowing through, or around, the devices to minimize or prevent formation of thrombus or other coagulation products on blood-contacting surfaces of the devices. In the preferred embodiment, the additional biologically compatible organic composition is heparin non-covalently combined with the substrate material and/or covering material. The heparin can be removed from the sterilized devices prior to packaging and storage (FIGS. 6B, 6C, 7B, and 7C) or allowed to remain with the sterilized devices. The preferred sterilization method includes ethylene oxide gas.

Figure 12:
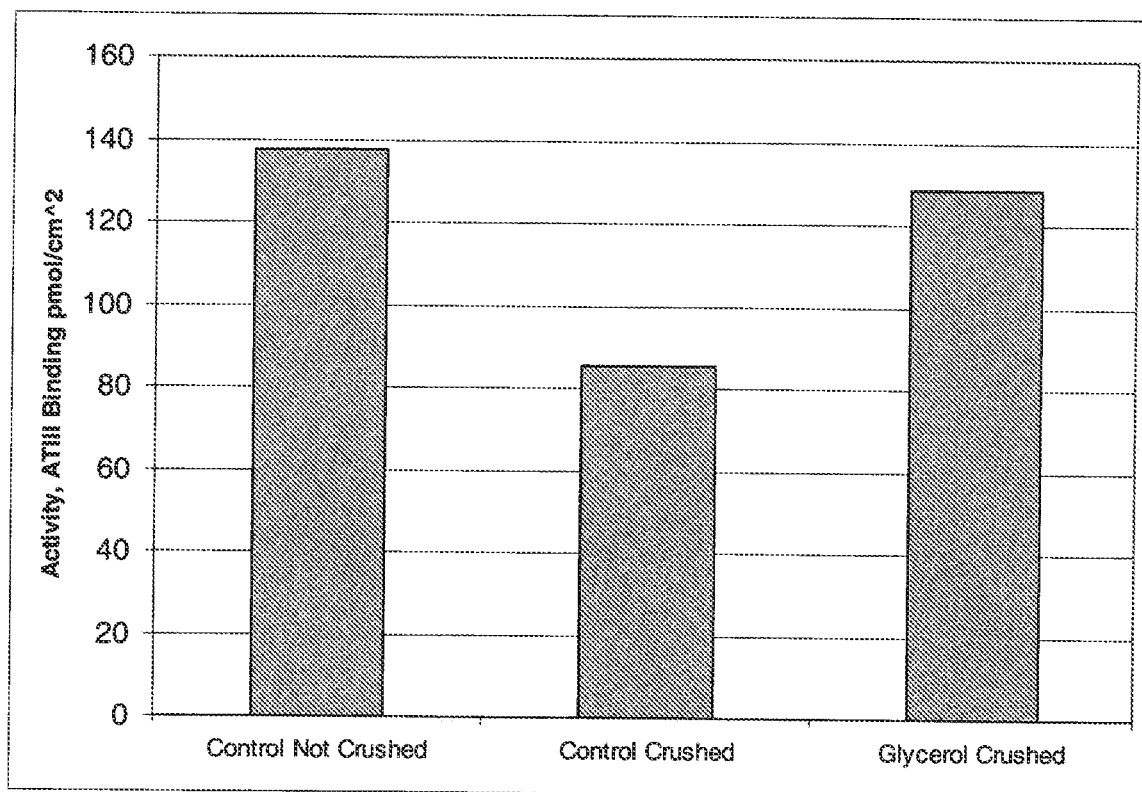
FIG. 12 is a bar graph illustrating the ability of added glycerol to maintain the biological activity of end-point attached heparin immobilized on a polymeric covering material of a substrate following compaction and expansion of the substrate material.
Figure 13:
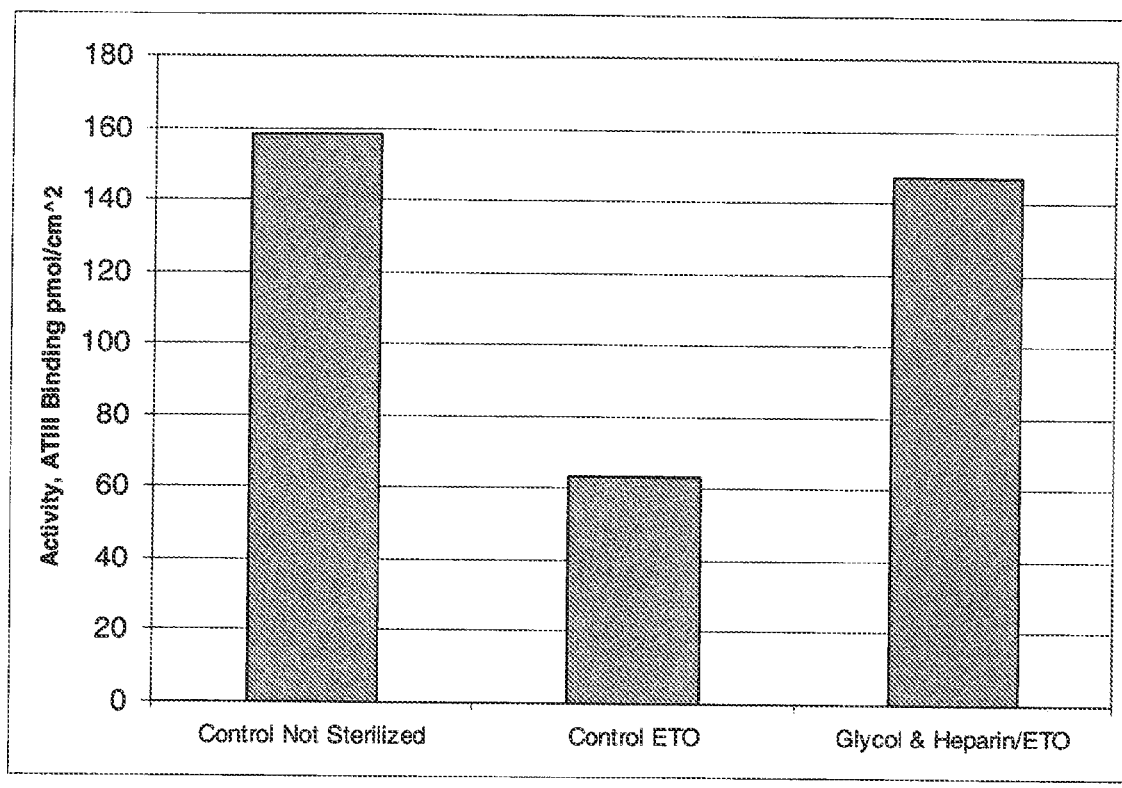
FIG. 13 is a bar graph illustrating the ability of added glycerol and heparin to maintain the biological activity of end-point attached heparin immobilized on a polymeric covering material of a substrate following compaction, exposure to an ethylene oxide sterilization regimen, and expansion of the substrate material.

Packaging of the sterilized devices may require mechanical manipulation that often reduces the biological activity of an immobilized biologically active entity. The additional biologically compatible composition combined with the immobilized biologically active entities, substrate material, and/or covering material as described above, also maintains the biological activity of the immobilized biologically active entities following compaction and expansion of a medical device (FIGS. 12 and 13). Expandable stents and stent-grafts are medical devices for which improved biological activity of immobilized biologically active entities is particularly significant.

The present invention, therefore, provides sterilized devices having biologically active entities immobilized thereto where the biological activity of the immobilized entities is significantly retained during and after a sterilization process (FIGS. 9-13). Prior to sterilization, the devices can be mechanically manipulated, through compaction and expansion, for example, and retain significant biological activity (FIGS. 12 and 13).

EXAMPLES

Except for Example 1, calculations of heparin activity on surfaces in the present invention were conducted using the surface area of only one side of the sample material, although the entire sample, including interstices, may have heparin immobilized thereon. The heparin activity was assayed by measuring the ability, or capacity, of the end-point attached heparin to bind a known quantity of anti-thrombin III (ATIII). The results were expressed as picomoles anti-thrombin III (ATIII) bound per square centimeter of substrate material (pmol ATIII/cm² substrate material). This assay is described by Larsen M. L., et al. in "Assay of plasma heparin using thrombin and the chromogenic substrate H-D-Phe-PipArg-pNA" (S-2238) (Thromb. Res. 1978; 13:285-288) and Pasche, et al. in "A binding of antithrombin to immobilized heparin under varying flow conditions" (Artif. Organs 1991; 15:281-491).

ATIII binding activity per surface area of substrate material is defined as the number of picomoles of ATIII bound per apparent surface area of covered or uncovered substrate material. The apparent substrate surface area does not take into account multiple covered surfaces nor porosity considerations of a porous substrate material. If the substrate material is porous, the effect of porosity on surface area is not considered for these calculations. For example, the apparent surface area of a cylindrical tubular ePTFE vascular graft (which is made of a porous material) with end-point attached heparin immobilized on substrate material comprising the inner surface of the tubular graft is calculated as it is for any cylindrical geometry as $2\pi rL$: where r is the graft inner radius; L is the axial length; and $\pi$ is the number pi. It is important to note that the porous nature of ePTFE and its effect on surface area is not accounted for herein. Accordingly, non-porous substrate materials that are cut into squares for analysis are taken to have a surface area of the length multiplied by the width.

Example 1

This example demonstrates retention of biological activity of unbound "neat" heparin following exposure of the heparin to an ethylene oxide (ETO) sterilization process.

In this example, unsterilized USP grade heparin-sodium in lyophilized powder form was obtained from Celsus Laboratories (Cincinnati, Ohio). Measured quantities of heparin were placed into CHEX-ALL® sterilization pouches (Long Island City, N.Y.) for testing. One group of heparin-containing pouches was exposed to ETO sterilization. Ethylene oxide sterilization was carried out under conditions of conditioning for one hour (1 hr), an ETO gas dwell time of one hour (1 hr), a set point temperature of fifty-five degrees centigrade (55° C.), and an aeration time of twelve hours (12 hr). Another group was subjected to the sterilization procedure in the absence of ETO. A third group was not exposed to the sterilization procedure.

Following the sterilization procedure, known quantities of heparin were removed from each pouch and tested for bioactivity with an ACTICHROME Heparin (anti-FXa) assay kit available from American Diagnostica Inc. (Stamford, Conn.). Bioactivity values for each heparin sample were expressed as international units of heparin per mass of heparin (IU/mg). International units of heparin are calculated based on Factor $X_a$ inactivation by ATIII that is catalyzed by heparin. International units are therefore a measure of the ATIII binding activity of heparin. Any reduction in heparin activity is expressed simply as a reduction in the IU/mg for comparable heparin controls from the ACTICHROME test. Heparin exhibiting a reduction in activity is considered to have been deactivated to a degree by the sterilization process.

Figure 8:
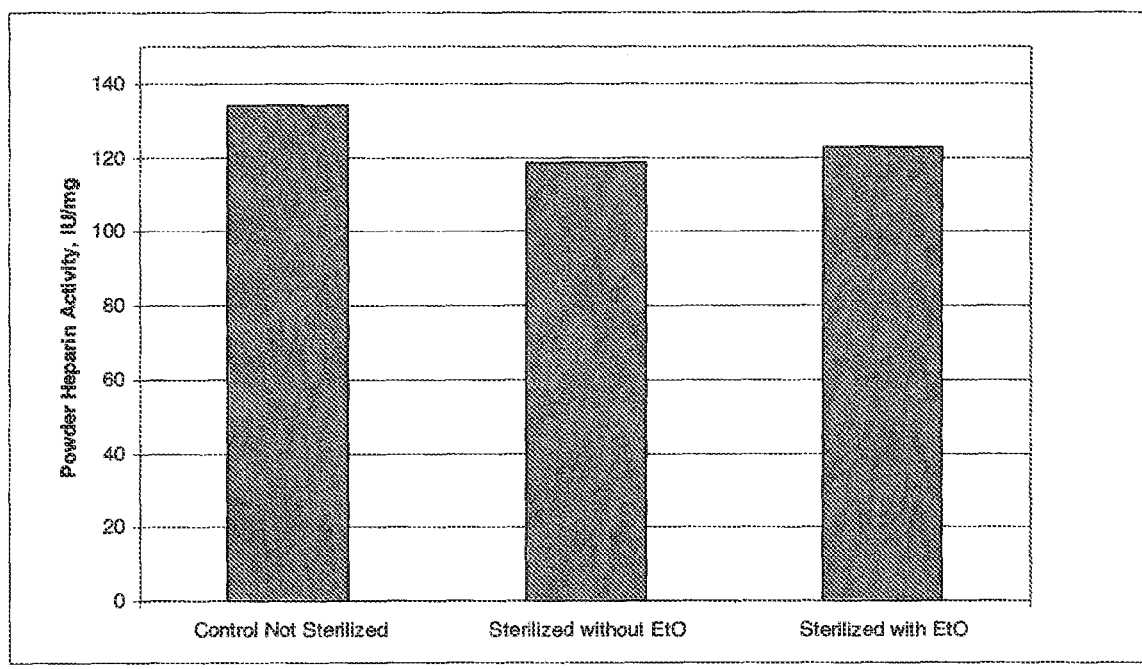
FIG. 8 is a bar graph illustrating how sterilization of unbound heparin does not significantly reduce the biological activity of the heparin.

FIG. 8 is a bar graph illustrating the effect of ETO sterilization on the anti-thrombin III (ATIII) binding activity of dry powdered heparin in an unbound state. FIG. 8 shows the mean activity levels, expressed as IU/mg, for the heparin samples (n=3) in each group. Control heparin samples that did not undergo sterilization had a mean value of 138 IU/mg. Control heparin samples that underwent the sterilization process in the absence of ETO (i.e., high humidity, high temperatures, etc.) had a mean value of 119 IU/mg. The heparin samples that underwent the sterilization process in the presence of ETO had a mean value of 123 IU/mg. The heparin samples exposed to the sterilization process in the absence of ETO had an eleven percent (11%) decrease in activity compared to the unsterilized control samples, while the samples exposed to the sterilization process in the presence of ETO had only an eight percent (8%) decrease in activity. As seen from FIG. 8, sterilization of unbound, neat, heparin powder in the presence or absence of ETO does not significantly reduce ATIII binding to the heparin when compared to unsterilized control samples. The anti-thrombin III binding activity of unbound, unsterilized, heparin is not significantly diminished by sterilization without ETO or sterilization with ETO. Therefore, degradation of the anti-thrombin III binding activity of immobilized heparin subjected to similar ETO sterilization conditions must be caused by a mechanism other than simple exposure to sterilization with or without ETO.

Example 2

This example describes the construction of an embodiment of the present invention in which heparin anti-thrombin III (ATIII) binding is not significantly diminished by exposure to ETO sterilization.

In accordance with U.S. Pat. No. 6,653,457, which is incorporated herein by reference, an aldehyde modified heparin composition made according to U.S. Pat. No. 4,613,665, which is incorporated herein by reference, was end-point attached to a covering material, or coating layer, placed on an expanded polytetrafluoroethylene (ePTFE) material. An additional biologically compatible organic composition was incorporated within the covering material and bound heparin to enable the immobilized heparin to undergo ETO sterilization without significant loss in biological activity.

An ePTFE material in sheet form was obtained from W. L. Gore & Associates, Inc., Flagstaff, Ariz. under the tradename GORE™ Microfiltration Media (GMM-406). A covering material in the form of a base coating was applied to the ePTFE material by mounting the material on a ten centimeter (10 cm) diameter plastic embroidery hoop and immersing the supported ePTFE material first in 100% isopropyl alcohol (IPA) for about five (5) minutes and then in a solution of LUPASOL® polyethylene imine (PEI) and IPA in a one to one ratio (1:1). LUPASOL® water-free PEI was obtained from BASF and diluted to a concentration of about four percent (4%) and adjusted to pH 9.6. Following immersion of the ePTFE material in the solution for about fifteen (15) minutes, the material was removed from the solution and rinsed in deionized (DI) water at pH 9.6 for fifteen (15) minutes. PEI remaining on the ePTFE material was cross-linked with a 0.05% aqueous solution of glutaraldehyde (obtained from Amresco) at pH 9.6 for fifteen (15) minutes. Additional PEI was added to the construction by placing the construction in a 0.5% solution of PEI at pH 9.6 for fifteen (15) minutes and rinsing again in DI water at pH 9.6 for fifteen (15) minutes. The imine formed as a result of the reaction between glutaraldehyde and the PEI layer is reduced with a sodium cyanborohydride ($NaCNBH_3$) solution (5 g dissolved in 1 L DI water, pH 9.6) and rinsed in DI water for thirty (30) minutes.

An additional layer of PEI was added to the construction by immersing the construction in 0.05% glutaraldehyde solution at pH 9.6 for fifteen (15) minutes, followed by immersion in a 0.5% solution of PEI at pH 9.6 for fifteen (15) minutes. The construction was then rinsed in DI water at pH 9.6 for fifteen (15) minutes. The resultant imines were reduced by immersing the construction in a solution of $NaCNBH_3$ (5 g dissolved in 1 L DI water, pH 9.6) for fifteen (15) minutes followed by a rinse in DI water for thirty (30) minutes. A third layer was applied to the construction by repeating these steps. The result was a porous hydrophobic fluoropolymeric base material having a hydrophilic cross-linked polymer base coat on substantially all of the exposed and interstitial surfaces of the base material.

An intermediate chemical layer was attached to the polymer base coat in preparation for placement of another layer of PEI on the construction. The intermediate ionic charge layer was made by incubating the construction in a solution of dextran sulfate (Amersham Pharmacia Biotech) and sodium chloride (0.15 g dextran sulfate and 100 g NaCl dissolved in 1 L DI water, pH 3) at 60° C. for ninety (90) minutes followed by rinsing in DI water for fifteen (15) minutes.

A layer of PEI, referred to herein as a "capping layer" was attached to the intermediate layer by placing the construction in a 0.3% aqueous solution of PEI (pH 9) for about forty-five (45) minutes followed by a rinse in a sodium chloride solution (50 g NaCl dissolved in 1 L DI water) for twenty (20) minutes. A final DI water rinse was conducted for (20) minutes.

Aldehyde modified heparin was end point attached, or conjugated, to the PEI layer(s) by placing the construction in a heparin-containing sodium chloride salt solution (1.5 g heparin, 29.3 g NaCl dissolved in DI water, pH 3.9) for one hundred twenty (120) minutes at sixty degrees centigrade (60° C.). A 2.86 mL volume of a 2.5% (w/v) aqueous $NaCNBH_3$ solution was added to the one liter (1 L) heparin solution prior to adding the samples. The samples were then rinsed in DI water for fifteen (15) minutes, borate buffer solution (10.6 g boric acid, 2.7 g NaOH and 0.7 g NaCl dissolved in 1 L DI water, pH 9.0) for twenty (20) minutes, and finally in DI water for fifteen (15) minutes followed by lyophilization of the entire construction to produce dry heparin bound to the ePTFE material. The presence and uniformity of the heparin was determined by staining samples of the construction on both sides with toluidine blue. The staining produced an evenly purpled surface indicating heparin was present and uniformly bound to the ePTFE material.

By adding particular compounds or compositions to the heparin-bound construction, the biological activity of the heparin can be maintained following exposure to conditions that would otherwise decrease the biological activity of the heparin. The conditions include, but are not limited to, ETO sterilization, mechanical crushing, packaging, and storage.

The above-described constructions coated with a covering material were exposed to solutions of the following compounds to evaluate their stabilizing effect on the biological activity of the heparin bound to parts of the coating: USP grade calcium chloride (Fisher Scientific), USP grade heparin sodium (Celsus), polyethylene glycol (20,000 molecular weight, Sigma), DEAE dextran (500,000 molecular weight, PK chemical), dextran sulfate sodium salt (8,000 molecular weight, Sigma), and dextran (9,500 molecular weight, Sigma) at concentrations of 0.5 g per 100 ml DI water adjusted to pH 9.6. Dexamethasone was also utilized at 0.5 g per 100 ml ethanol with no pH adjustment. Each of these solutions is referred to herein as a "treatment solution." The effect of these various compounds on binding activity of heparin to anti-thrombin III (ATIII) following ETO sterilization was expressed as picomoles anti-thrombin III bound per square centimeter ($cm^2$) substrate material. These data are summarized in FIG. 9.

To expose a particular heparin-containing construction to a particular treatment solution, the construction was placed into a two liter (2 L) beaker and one hundred milliliters (100 ml) of treatment solution was added, sufficient to completely immerse the construction in the treatment solution. Each construction was exposed to the treatment solution for one hour (1 hr) at sixty degrees centigrade (60° C.). The construction was removed from the solution and lyophilized prior to exposure to a sterilization procedure.

In preparation for ETO sterilization, each lyophilized construction was placed and sealed in a Tower DUALPEEL® Self-Seal Pouch (Alligiance Healthcare Corp., McGraw Park, Ill.). Ethylene oxide sterilization was carried out under conditions of conditioning for one hour (1 hr), an ETO gas dwell time of one hour (1 hr), a set point temperature of fifty-five degree centigrade (55° C.), and an aeration time of twelve hours (12 hrs).

After ETO sterilization, each construction (including controls) was removed from its pouch and washed in DI water for fifteen (15) minutes, borate buffer solution (10.6 g boric acid, 2.7 g NaOH and 0.7 NaCl dissolved in DI water, pH 9.0) for twenty (20) minutes, and finally a rinse in DI water for fifteen (15) minutes.

Samples approximately one square centimeter (1 cm$^2$) in size were cut from the construction and assayed for heparin activity by measuring the capacity of the end point attached heparin to bind ATIII. The assay is described by Larsen M. L., et al., in "Assay of plasma heparin using thrombin and the chromogenic substrate H-D-Phe-Pip-Arg-pNA (S-2238)." Thromb Res 13:285-288 (1978) and Pasche B., et al., in "A binding of antithrombin to immobilized heparin under varying flow conditions." Artif. Organs 15:281-491 (1991). The results were expressed as amount of ATIII bound per unit surface area substrate material in picomoles per square centimeter (pmol/cm$^2$). All samples were maintained in a wet condition throughout the assay. It is important to note that while the approximately one square centimeter (1 cm$^2$) samples each have a total surface area of two square centimeters (2 cm$^2$) if both sides of the material are considered, only one surface on the sample (i.e., 1 cm$^2$) was used for calculating ATIII heparin-binding activity in pmol/cm$^2$.

Figure 9:
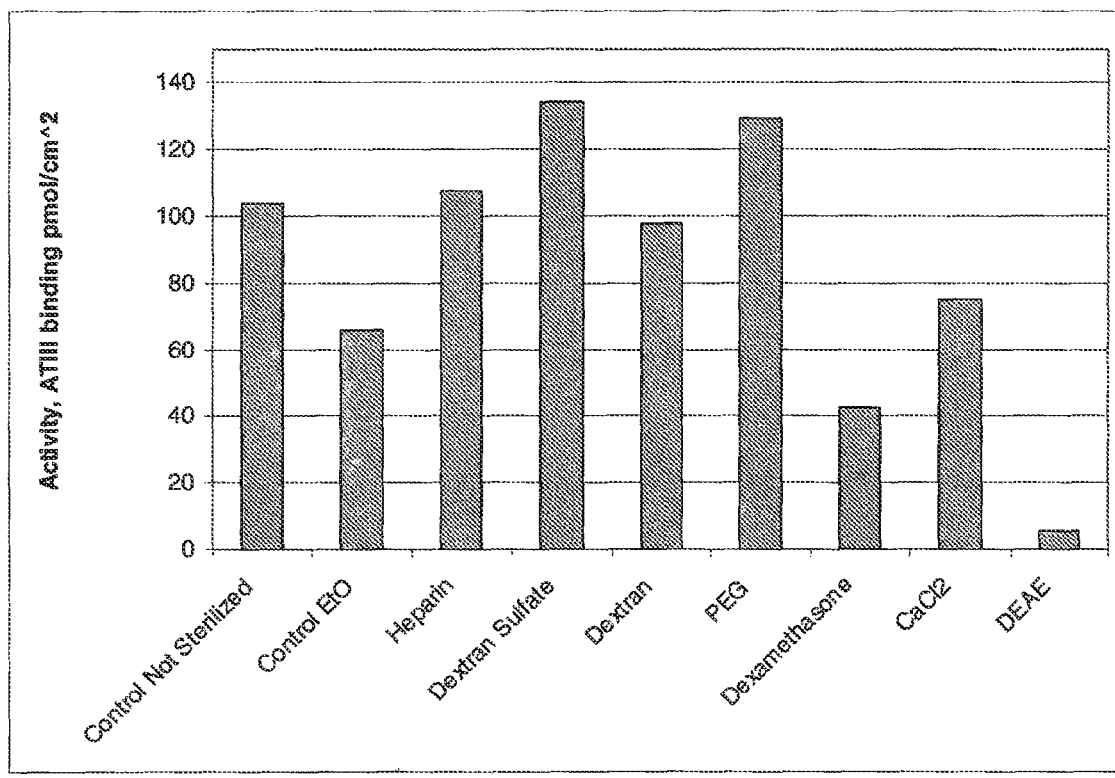
FIG. 9 is a bar graph illustrating the effect of a variety of biologically compatible organic compositions on the biological activity of end-point attached heparin immobilized to reactive chemical groups on a polymeric covering material during and after exposure of the immobilized heparin to an ethylene oxide sterilization regimen.

FIG. 9 is a bar graph illustrating the effects various biologically compatible organic compositions non-covalently combined with heparin immobilized on a covered substrate material on the anti-thrombin III binding activity of the immobilized heparin following exposure of the immobilized heparin to ETO sterilization.

The anti-thrombin III binding activity to the immobilized heparin was expressed in picomoles ATIII bound per square centimeter of substrate material (pmol/cm$^2$). One set of control samples were not sterilized. Another set of control samples were subjected to ETO sterilization in the absence of a biologically compatible organic composition non-covalently combined with the immobilized heparin and covering material. Each remaining bar represents the anti-thrombin III binding activity of immobilized heparin in the presence of the indicated biologically compatible organic composition non-covalently combined with the immobilized heparin and covering material. All bars represent mean values of n=3 samples, except for dextran sulfate with n=6 samples.

As can be seen from the bar graph, sterilized control samples showed a dramatic reduction in anti-thrombin III binding activity compared to unsterilized control samples. The anti-thrombin III binding activity of the unsterilized control samples was 103 pmol/cm$^2$ substrate material. The anti-thrombin III binding activity of the sterilized control samples was 66 pmol/cm$^2$ substrate material. ETO sterilization caused a thirty-six percent (36%) reduction in anti-thrombin III binding activity compared to the unsterilized samples.

The influence of the following biologically compatible organic compositions non-covalently combined with the immobilized heparin and covering material on the anti-thrombin III binding activity is summarized as follows. Each biologically compatible organic composition was rinsed, as described earlier, from each construction before the anti-thrombin III binding activity was determined.

When heparin was added to the construction, the mean anti-thrombin III binding activity was 108 pmol/cm$^2$. Addition of dextran to the construction resulted in a mean anti-thrombin III binding activity of 98 pmol/cm$^2$ substrate material. When dextran sulfate was added to the construction, the mean anti-thrombin III binding activity was 134 pmol/cm$^2$ substrate material. Additionally, polyethylene glycol resulted in a mean anti-thrombin III binding activity of 129 pmol/cm$^2$ substrate material. Interestingly, these values are greater than the mean values for the unsterilized control samples at 103 pmol/cm$^2$ substrate material.

When inorganic calcium chloride ($CaCl_2$) was added to the construction, the mean anti-thrombin III binding activity of the immobilized heparin was 75 pmol/cm$^2$ substrate material. Addition of dexamethasone to the construction resulted in a mean anti-thrombin III binding activity of 42 pmol/cm$^2$ substrate material. DEAE dextran seemed to diminish the anti-thrombin III binding activity of the immobilized heparin with a mean activity of 5 pmol/cm$^2$ substrate material.

These results demonstrate the ability to maintain, or increase, the anti-thrombin III binding activity of end point attached heparin following ETO sterilization with an appropriate biologically compatible composition non-covalently combined with the immobilized heparin and covering material.

Example 3

This example describes the ability of an additional biologically compatible organic composition to produce a high anti-thrombin III (ATIII) binding activity of heparin end point attached to a polymeric covering material on a substrate material that is a component of an implantable medical device.

The implantable medical device used in this example was in the form of a nitinol wire reinforced tube made of a porous, expanded, polytetrafluoroethylene (ePTFE) material obtained from W. L. Gore & Associates, Inc., Flagstaff, Ariz. under the tradename VIABAHN® Endoprosthesis. The tubular device was fifteen centimeters (15 cm) in length and six millimeters (6 mm) in diameter.

The VIABAHN® Endoprosthesis was constrained within a delivery catheter and required removal from the catheter before immobilizing heparin thereon. Each catheter-constrained device was removed for processing by pulling a release cord attached to a constraining sheath and releasing the sheath from around the device. Once unconstrained, each device was expanded and used as a separate substrate material. Each substrate material (endoprosthetic device) was immersed in a PEI solution (5% in DI water, pH9.6) and IPA in a volume percent ratio of 30:70, respectively, for about twelve hours (12 hr.) to place a polymeric covering material (18) on the substrate material (12). The polymeric covering material (18) had a multiplicity of reactive chemical groups (16) to which a plurality of aldehyde-modified heparin molecules (17) were eventually end point attached.

At least one additional layer of covering material (18a, 18b) was placed on the first PEI layer (18). This was performed by placing each endoprosthetic device within a separate silicone tube and the tube connected to a peristaltic pump and solution-reservoir. This allowed an additional solution containing a covering material to be repeatedly passed through the center of the tubular medical device to coat primarily the inside surfaces of the device.

With each endoprosthesis contained within one of these dynamic flow systems, a covering material (18) in the form of a solution of 0.10% (pH 9.0) PEI and IPA in a volume percent ratio of 45:55, respectively, was passed through the device for about twenty (20) minutes. Each device was then rinsed in DI water (pH 9.0) for five minutes (5 min) and the PEI layers cross-linked (19) by exposure to a 0.05% aqueous glutaraldehyde solution (pH 9.0) for twenty (20) minutes. The devices were then rinsed again with a solution of PEI (0.10%, pH 9.0) for two and a half minutes (2.5 min). The resultant imines were reduced with a sodium cyanborohydride solution (5 g in 1 L DI water, pH 9.0) for fifteen minutes (15 min) and rinsed in DI water for thirty (30) minutes.

An intermediate ionic charge layer was placed on the cross-linked PEI layer(s) of each device by flowing a solution of dextran sulfate (0.15 g dextran sulfate and one hundred grams sodium chloride (10 g NaCl) dissolved in one liter (1 L) of DI water, pH3) through the dynamic flow system and over the PEI layer at sixty degrees centigrade (60° C.) for about ninety (90) minutes. This was followed by rinsing the system with DI water for fifteen (15) minutes.

A "capping" layer (18b) of PEI was added to the ionically charged dextran sulfate layer (18a) by flowing a solution of PEI (0.075%, pH9.0) through the dynamic flow system for about forty-five (45) minutes followed by a rinse in a sodium chloride solution (50 g NaCl dissolved in 1 L DI water) for fifteen (15) minutes. The rinse was followed by a brief DI water flush for about two and a half (2.5) minutes.

Aldehyde modified heparin was end point attached, or conjugated, to the PEI layer(s) by placing the construction in a heparin-containing sodium chloride salt solution (1.5 g heparin, 29.3 g NaCl dissolved in DI water, pH 3.9) for one hundred twenty (120) minutes at sixty degrees centigrade (60° C.). A 2.86 mL volume of a 2.5% (w/v) aqueous NaCNBH$_3$ solution was added to the one liter (1 L) heparin solution prior to beginning this step. A first rinse in DI water for fifteen (15) mintues, was followed by a rinse in a boric acid solution (0.7 g NaCl, 10.6 g boric acid and 2.7 g NaOH dissolved in 1 L DI water, pH 9.0) for about twenty (20) minutes, and a final rinse in DI water for fifteen (15) minutes. The construction was then subjected to a lyophilization process. Staining of selected samples with toluidine blue produced a consistent purple surface indicating uniformly bound heparin.

Based on the results obtained in the studies described in Example 2, supra, USP grade heparin (sodium salt) and 8,000 MW dextran sulfate (sodium salt) at a concentration of 0.5 g/100 ml DI water (pH9.6), were chosen as the preferred biologically compatible organic compositions to maintain, or stabilize, the anti-thrombin III binding activity of the immobilized heparin during and after ETO-sterilization.

For each preferred biologically compatible organic composition, sections of the endoprostheses having heparin endpoint attached to a polymeric covering material were placed in plastic tubes containing a solution of said biologically compatible organic compositions (each at a concentration of 0.5 g/100 mL DI water, pH 9.6) and incubated at sixty degrees centigrade (60° C.) for one hour (1 hr). Each treated sample was removed from the plastic tube and exposed to a lyophilization process.

Each lyophilized sample was placed in an individual Tower DUALPEEL® Self Sealing Pouch (Alligiance Healthcare Corp., McGraw Park, Ill.) and sealed for ETO sterilization. Ethylene oxide sterilization was carried out under conditions of conditioning for one hour (1 hr), an ETO gas dwell time of one hour (1 hr), a set point temperature of fifty-five degrees centigrade (55° C.), and an aeration time of twelve (12) hours.

After ETO sterilization, each construction was removed from its pouch and washed in DI water for fifteen (15) minutes, borate buffer solution (10.6 g boric acid 2.7 g NaOH and 0.7 g NaCl dissolved in DI water, pH 9.0) for twenty (20) minutes, and finally a rinse in DI water for fifteen (15) minutes.

Samples of substrate material from each ETO-sterilized device (approx. 0.5 cm long) were cut from each device and the immobilized heparin measured for biological activity using the above-described ATIII binding assay (Example 2). Samples were kept wet throughout the assay process. The results were expressed as picomoles of anti-thrombin III bound per area unit of substrate material (pmol/cm$^2$) as measured on the luminal surface of each device and not the entire surface area of the device (i.e., both abluminal and luminal surfaces).

Figure 10:
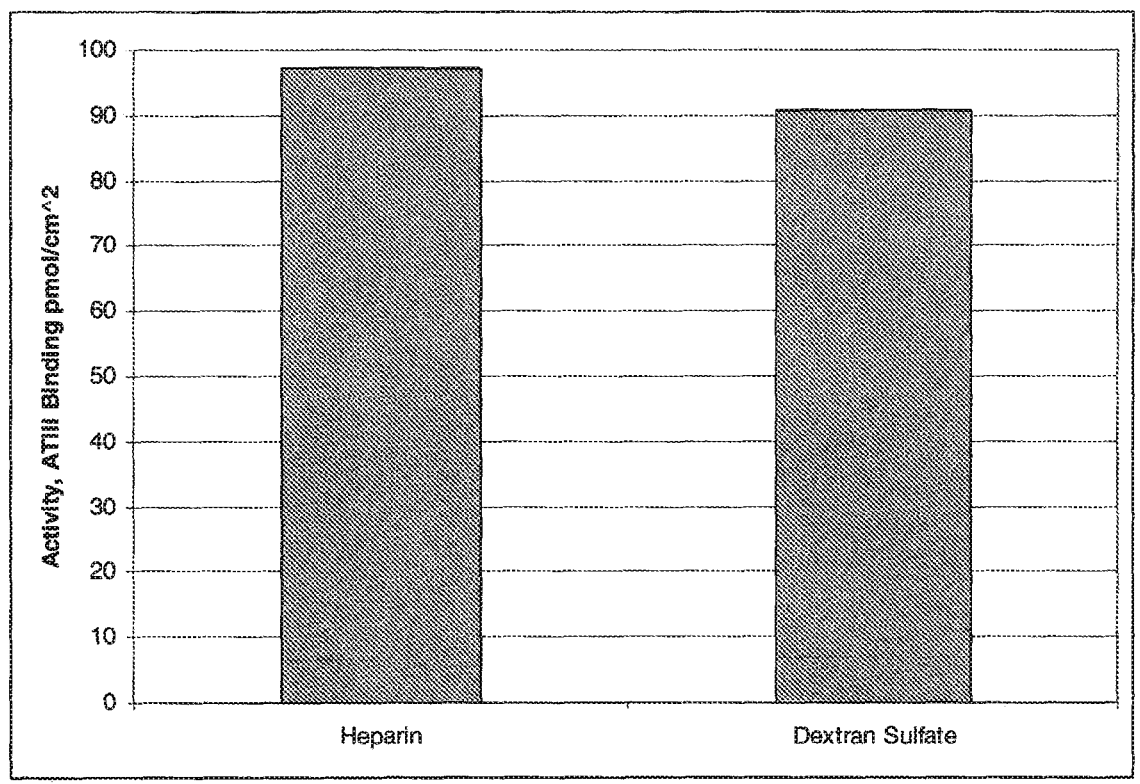
FIG. 10 is a bar graph illustrating the ability of added heparin or dextran sulfate biologically compatible organic compositions to result in high levels of ATIII binding activity of heparin immobilized to a polymeric covering material on a substrate during and after exposure of the immobilized heparin to an ethylene oxide sterilization regimen.

FIG. 10 is a bar graph illustrating the effect of two separate biologically compatible organic compositions in the form of heparin and dextran sulfate on anti-thrombin III binding activity of heparin immobilized on a covered substrate material during and after exposure to an ETO sterilization regimen. Anti-thrombin III binding activity is expressed as picomoles of bound anti-thrombin III per square centimeter of substrate material. As seen from the results, the use of heparin and dextran sulfate biologically compatible organic compositions resulted in high anti-thrombin III binding activity to immobilized heparin following ETO sterilization, with activities of 97 pmol/cm$^2$ substrate material and 91 pmol/cm$^2$ substrate material, respectively. All bars represent mean values of n=6 samples.

Example 4

This example describes construction of an embodiment of the present invention having an aldehyde modified heparin compound end point attached to a polymeric covering material that includes an ionically neutral first covering layer. The construction had heparin ATIII binding that was not significantly diminished by exposure to ETO sterilization.

The covering material used as a base coat in this construction was chosen to render a heparin-containing covering material, or coating, that had essentially no ionic charge. Polyvinyl alcohol and PEI were used as the covering materials.

In accordance with U.S. Pat. No. 6,653,457, which is incorporated herein by reference, an aldehyde modified heparin composition was bound to a covered substrate material. The substrate material (12) was expanded polytetrafluoroethylene (ePTFE) material. An additional biocompatible organic chemical composition (100) was incorporated into the heparin-containing covering material (18) of the construction to enable the heparin to undergo ETO sterilization without significant loss in biological activity.

An ePTFE substrate material in sheet form was obtained from W. L. Gore & Associates, Inc., Flagstaff, Ariz. under the tradename GORE™ Microfiltration Media (GMM-406). A layer of covering material, or base coat, was applied to the ePTFE substrate material by mounting the material on a 10 cm diameter plastic embroidery hoop and immersing the supported ePTFE material in a solution of 100% IPA for about five (5) minutes. This was followed by immersion of the ePTFE material in an aqueous two percent (2%) solution of USP grade polyvinyl alcohol (PVA) (Spectrum) for fifteen (15) minutes. After a fifteen (15) minute rinse in DI water, the PVA layer was exposed to a solution of two percent (2%) glutaraldehyde and one percent (1%) hydrochloric acid (HCL) for fifteen (15) minutes to cross-link (19) the PVA (18), in situ. The construction was rinsed in DI water for fifteen (15) minutes followed by a second fifteen (15) minute DI water rinse. The resulting cross-linked PVA base coating had no net ionic charge.

Another layer of polymeric covering material (18a) was added to the construction by immersing the construction in an aqueous 0.15% solution of PEI (pH 10.5) solution for thirty (30) minutes. The resultant imines were reduced by immersing the construction in an aqueous solution of sodium cyanoborohydride solution (5 gm/L in DI water, pH 10.5) for fifteen (15) minutes. The construction was rinsed in DI water for fifteen (15) minutes followed by a second fifteen (15) minute DI water rinse.

A covered ePTFE substrate material having a multiplicity of reactive chemical groups thereon was immersed in the heparin solution (1.0 g heparin, 29.3 g NaCl dissolved in DI water, pH 3.9) for 90 minutes at 60° C. A 2.86 mL volume of a 2.5% (w/v) aqueous $NaCNBH_3$ solution was added to the 1 L heparin solution prior to beginning this step. A first fifteen (15) minute rinse in DI water, was followed by a rinse in an aqueous boric acid solution (0.7 g NaCl, 10.6 g boric acid, 2.7 g NaOH dissolved in 1 L DI water, pH 9.0) for about twenty (20) minutes, and a final rinse in DI water rinse for fifteen (15) minutes. The construction was then subjected to a lyophilization process. Samples of the construction were then stained with toluidine blue. The staining produced a consistent purple surface indicating uniformly bound heparin on the covered ePTFE material.

The construction was exposed to an aqueous treatment solution containing a biologically compatible organic composition (100) in the form of 8,000 MW USP grade dextran sulfate (sodium salt) (Sigma) by immersing the construction in 100 ml treatment solution (0.5 g of dextran sulfate/100 mL DI water, pH 9.6) at sixty degrees centigrade (60° C.) for one (1) hour. Following removal of the construction from the treatment solution, the construction was lyophilized.

Each lyophilized construction was placed in a Tower DUALPEEL® Self Seal Pouch (Alligiance Healthcare Corp., McGraw Park, Ill.) for ETO sterilization. Ethylene oxide sterilization was carried out under conditions of conditioning for one hours (1 hr), an ETO gas dwell time of one hour (1 hr), a set point temperature of fifty-five degrees centigrade (55° C.), and an aeration time of twelve (12) hours.

After ETO sterilization, each construction (including controls) was removed from its pouch and washed in DI water for fifteen (15) minutes, a borate buffer solution (10.6 g boric acid, 2.7 g NaOH, 0.7 g NaCl, pH 9.0) for twenty (20) minutes, and finally a rinse in DI water for fifteen (15) minutes.

Samples of the membrane (approx. 1 $cm^2$) with end-point attached heparin were cut and the immobilized heparin measured for anti-thrombin III binding activity using the above-described ATIII binding assay (Example 2). Samples were kept wet throughout the assay process. The results were expressed as picomoles of anti-thrombin III bound per unit of substrate surface area ($pmol/cm^2$ substrate material).

Figure 11:
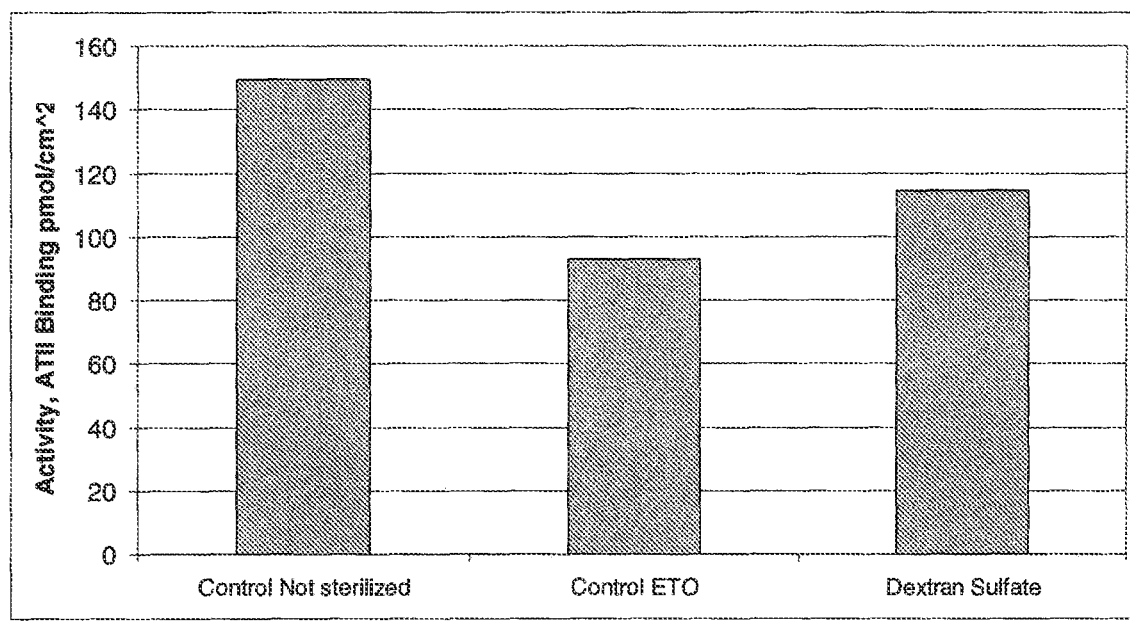
FIG. 11 is a bar graph illustrating the ability of added dextran sulfate to maintain the biological activity of end-point attached heparin immobilized on a polyvinyl alcohol coated substrate during and after exposure of the immobilized heparin to an ethylene oxide sterilization regimen.

FIG. 11 is a bar graph illustrating the effect of a biologically compatible organic composition in the form dextran sulfate on anti-thrombin III binding activity of end-point attached heparin immobilized on a porous expanded polytetrafluoroethylene substrate material and a covering material of polyvinyl alcohol and PEI, following ETO sterilization. The biological activity of the immobilized heparin was expressed as picomoles of anti-thrombin III bound per square centimeter of substrate material.

Unsterilized control samples had an anti-thrombin III binding activity of 150 $pmol/cm^2$ substrate material. The sterilized control samples had an anti-thrombin III binding activity of 93 $pmol/cm^2$ substrate material. Ethylene oxide sterilized samples treated with dextran sulfate had an anti-thrombin III binding activity of 115 $pmol/cm^2$ substrate material. This value was greater than the control values for ETO-sterilized devices which were not exposed to a dextran sulfate treatment solution (i.e., 93 $pmol/cm^2$ substrate material), indicating the added dextran sulfate increased the biological activity of the immobilized heparin following ETO sterilization. Both of these constructions had anti-thrombin III binding activity values that were significantly lower than the non-treated, non-ETO sterilized, controls (150 $pmol/cm^2$ substrate material).

As seen from the results, dextran sulfate significantly impacted the anti-thrombin III binding activity of the immobilized heparin attached to a construction with a polymeric covering material that includes an ionically neutral first covering layer, following ETO sterilization. All bars represent mean values of n=3 samples.

Example 5

This example describes the ability of an additional biologically compatible organic composition to maintain or increase the biological activity of a biologically active heparin immobilized to a covered substrate material during and after imposition of a mechanical stress of sufficient magnitude to otherwise significantly reduce the biological activity of the entity.

In this example, implantable medical devices in the form of endoluminal prostheses were provided with a heparin-containing coating as described in Example 3, supra. Each prosthesis was in the form of a nitinol wire reinforced tube made of a porous, expanded, polytetrafluoroethylene (ePTFE) material obtained from W. L. Gore & Associates, Inc., Flagstaff, Ariz. under the tradename VIABAHN® Endoprosthesis. The tubular device was fifteen centimeters (15 cm) in length and six millimeters (6 mm) in diameter. The same process was utilized as detailed in Example 3 for forming a heparin-containing coating on the device.

For treatment with the biologically compatible organic composition (100), substrate material (12) of the endoluminal device was prepared with a polymeric covering material (18) having aldehyde modified heparin (17) end point attached to at least a portion thereof. Sections of the prepared device were placed in plastic tubes and incubated with a glycerol solution (5 mL Sigma-Aldrich SigmaUltra glycerol in 100 mL of DI water, pH 9.6) at sixty degrees centigrade (60° C.) for one hour (1 hr). Each treated device was removed from the plastic tube and exposed to a lyophilization process.

Each cylindrical endoprosthesis was placed over an intravascular delivery system and mechanically compressed until it was sufficiently compacted on the delivery system to be restrained with a constraining sheath. Devices made according to Example 3 can withstand the mechanical stresses associated with compaction of the endoprosthesis on the delivery system without significant loss in the activity of the heparin incorporated in the coating.

Glycerol was chosen as the non-covalently bound biologically compatible organic composition (100) to maintain the biological activity of the end point attached heparin (17) during diametrical compaction and expansion of each test endoprosthesis. Each control endoprosthesis device section did not have the non-covalently bound biologically compatible glycerol composition (100) included with the end point attached (i.e., covalently bound) heparin (17) and polymeric covering material (18). Each device was subjected to a lyophilization process.

To compress and compact the endoluminal devices on a delivery system, each endoprosthesis was pulled through a tapered funnel with a fixed diameter. Each endoprosthesis had six (6) sutures (Gore-Tex® CV-0, 0N05) sewn through one end to pull the devices through the funnel. Each device was pulled through the opening of a twenty-five milliliter (25 ml) pipet tip (Falcon®, product #357525) with a diameter of about three millimeters (3 mm) and into a glass tube with a diameter of about 3.1 mm to hold it in the compacted state.

After compaction, each endoprosthesis was deployed in a 0.9% aqueous saline solution at thirty-seven degree centigrade (37° C.), rinsed and tested for anti-thrombin III binding activity as described herein. The results are shown in FIG. 12. Each endoprosthesis was prepared for testing by washing in DI water for fifteen (15) minutes, followed by a rinse in borate buffer solution (10.6 g boric acid 2.7 g NaOH, 0.7 NaCl, dissolved in 1 L of DI water, pH 9.0) for twenty (20) minutes and a final fifteen (15) minute DI water rinse.

Samples of heparin-containing material from each endoprosthesis (approx. 0.5 cm long) were cut and the bound heparin measured for biological activity using the above-described anti-thrombin III (ATIII) binding assay (Example 2). Samples were kept wet throughout the assay process. The results were expressed as anti-thrombin III binding per unit of substrate surface area (pmol/cm$^2$ substrate material).

FIG. 12 is a bar graph illustrating the effect of a glycerol composition with immobilized heparin on a covered substrate material following compaction and expansion. Results show that the addition of glycerol to immobilized heparin significantly improves the anti-thrombin III binding activity of the bound heparin following compaction and expansion of the immobilized heparin compared to similarly treated control samples not having the added glycerol. All vertical bars represent mean values of n=3 samples.

Heparin-immobilized to a polymeric covering material that did not receive the additional glycerol biologically compatible organic composition, and was diametrically compacted and expanded, showed a significant reduction in anti-thrombin III binding activity (85 pmol/cm$^2$) compared to similarly constructed and treated control materials not diametrically compacted and expanded (137 pmol/cm$^2$). When heparin-immobilized covered substrate materials were treated with a biologically compatible organic glycerol composition and exposed to the same mechanical manipulations as the untreated construction, the anti-thrombin III binding activity of the immobilized heparin remained similar to the control materials (129 pmol/cm$^2$).

Example 6

This example describes the effect of the addition of a biologically compatible organic composition on the ATIII binding activity of the coated medical device described in Examples 3 and 5, subjected to compaction, expansion and ETO sterilization.

The implantable medical device used in this example was constructed in the same way as described in Example 3. The device was in the form of a nitinol wire reinforced tube made of a porous, expanded, polytetrafluoroethylene (ePTFE) material obtained from W. L. Gore & Associates, Inc., Flagstaff, Ariz. under the tradename VIABAHN® Endoprosthesis. The tubular device was fifteen centimeters (15 cm) in length and six millimeters (6 mm) in diameter. The same process was utilized as detailed in Examples 3 for forming a heparin-containing coating on the device.

For treatment with the biologically compatible organic composition (100), substrate material (12) of the endoluminal device was prepared with a polymeric covering material (18) having aldehyde modified heparin (17) end point attached to at least a portion thereof. The prepared device was placed in a plastic tube and incubated with a heparin and glycerol solution (0.5 g USP heparin and 5 mL glycerol dissolved in 100 mL of DI water, pH 9.6) at sixty degrees centigrade (60° C.) for one hour (1 hr). The choice of these compounds is a result of the outcome of Examples 2, 3 and 5. Each treated device was removed from the heparin and glycerol solution and exposed to a lyophilization process. Further processing and analysis of devices was identical to Example 5, supra.

FIG. 13 is a bar graph illustrating the ability of a biologically compatible organic composition in the form of glycerol and heparin to maintain the biological activity of heparin immobilized to a polymeric covering material on a substrate material both during and after exposure to an ETO sterilization regimen and mechanic manipulation in the form of compaction and expansion of the substrate and polymeric covering material to which the heparin was immobilized. All vertical bars represent mean values of n=3 samples.

Heparin-immobilized covered substrate materials that did not receive the additional glycerol and heparin biologically compatible organic compositions and were exposed to ETO sterilization and diametrically compacted and expanded showed a significant reduction in anti-thrombin III binding activity (63 pmol/cm$^2$) compared to similarly constructed and treated control materials not subjected to ETO sterilization and diametrical compaction and expansion (158 pmol/cm$^2$). When heparin-immobilized covered substrate materials were treated with a biologically compatible organic glycerol and heparin composition and exposed to the same ETO sterilization conditions and mechanical manipulations as the untreated construction, the anti-thrombin III binding activity of the immobilized heparin remained similar to the control materials (147 pmol/cm$^2$).

Example 7

This example demonstrates a relatively low anti-thrombin III binding activity of a commercially available heparin-coated medical device. The device was a fifty centimeter (50 cm) long, six millimeter (6 mm) diameter, sterilized, and packaged heparin-coated vascular graft available under the tradename FLOWLINE BIPORE® Heparin Coated Vascular Graft (Catalog Number 15TW5006N) from JOTEC GmbH (Hechingen, Germany). According to the manufacturer, the tubular vascular graft is made of an expanded polytetrafluoroethylene (ePTFE) material with heparin covalently and ionically attached to the luminal surface of the graft. The manufacturer states that the heparin is stably and permanently attached to the ePTFE. Surfaces of the heparin-containing graft are said to be anti-thrombotic.

Samples (0.5 cm long) of the heparin-containing vascular graft were obtained and tested as described Example 2, supra. As with the inventive materials, the anti-thrombin III binding activity of the vascular graft were expressed as picomoles anti-thrombin III binding activity per square centimeter of substrate material (pmol/cm$^2$). As in previous examples, only the luminal surface area of each device was measured, not the entire surface area of the device. The results of the ATIII binding assay showed that there was no anti-thrombin III binding activity despite the claims by the manufacturer that biologically active heparin was present on luminal surface of the vascular graft. It should be noted that the anti-thrombin III binding activity assay is capable of detecting anti-thrombin III binding activity at a level of approximately five picomoles per square centimeter substrate material (5 pmol/cm² substrate material) and above.

The invention claimed is:

1. A sterilized medical device comprising:
   a fluoropolymeric substrate material;
   a polymeric covering material comprising imine groups that is attached to at least a portion of a surface of said substrate material, a plurality of biologically active entities having anti-thrombin III binding activity covalently attached to at least a portion of said polymeric covering material, wherein said plurality of biologically active entities comprises polysaccharides; and
   a biologically compatible organic composition non-covalently combined with said biologically active entities, wherein said biologically compatible organic composition comprises a carbohydrate,
   wherein said biologically active entities have an anti-thrombin III binding activity of at least 5 picomoles anti-thrombin III per square centimeter (pmol/cm²) substrate material following ethylene oxide sterilization of said biologically active entities.

2. The sterilized medical device of claim 1 wherein said plurality of biologically active entities comprises a glycosaminoglycan.

3. The sterilized medical device of claim 1 wherein said plurality of biologically active entities comprises end-point attached heparin.

4. The sterilized medical device of claim 1 wherein at least a portion of said biologically compatible organic composition is released from said sterilized medical device in a 0.15M phosphate buffer solution having a temperature of about thirty-seven degrees centigrade and a substantially neutral pH.

5. The sterilized medical device of claim 1 wherein said biologically compatible organic composition is a polysaccharide.

6. The sterilized medical device of claim 5 wherein said polysaccharide comprises a glycosaminoglycan.

7. The sterilized medical device of claim 6 wherein said glycosaminoglycan is heparin.

8. The sterilized medical device of claim 5 wherein said polysaccharide is dextran.

9. The sterilized medical device of claim 5 wherein said polysaccharide is dextran sulfate.

10. The sterilized medical device of claim 1 wherein said plurality of biologically active entities have an anti-thrombin III binding activity of at least 6 picomoles anti-thrombin III per square centimeter (pmol/cm²) substrate material following sterilization of said biologically active entities.

11. The sterilized medical device of claim 10 wherein said plurality of biologically active entities comprises a glycosaminoglycan.

12. The sterilized medical device of claim 10 wherein said plurality of biologically active entities comprises end-point attached heparin.

13. The sterilized medical device of claim 10 wherein at least a portion of said biologically compatible organic composition is released from said sterilized medical device in a 0.15M phosphate buffer solution having a temperature of about thirty-seven degrees centigrade and a substantially neutral pH.

14. The sterilized medical device of claim 1 wherein said plurality of biologically active entities have an anti-thrombin III binding activity of at least 7 picomoles anti-thrombin III per square centimeter (pmol/cm²) substrate material following sterilization of said biologically active entities.

15. The sterilized medical device of claim 14 wherein said plurality of biologically active entities comprises a glycosaminoglycan.

16. The sterilized medical device of claim 14 wherein said plurality of biologically active entities comprises end-point attached heparin.

17. The sterilized medical device of claim 14 wherein at least a portion of said biologically compatible organic composition is released from said sterilized medical device in a 0.15M phosphate buffer solution having a temperature of about thirty-seven degrees centigrade and a substantially neutral pH.

18. The sterilized medical device of claim 1 wherein said plurality of biologically active entities have an anti-thrombin III binding activity of at least 8 picomoles anti-thrombin III per square centimeter (pmol/cm²) substrate material following sterilization of said biologically active entities.

19. The sterilized medical device of claim 18 wherein said plurality of biologically active entities comprises a glycosaminoglycan.

20. The sterilized medical device of claim 18 wherein said plurality of biologically active entities comprises end-point attached heparin.

21. The sterilized medical device of claim 18 wherein at least a portion of said biologically compatible organic composition is released from said sterilized medical device in a 0.15M phosphate buffer solution having a temperature of about thirty-seven degrees centigrade and a substantially neutral pH.

22. The sterilized medical device of claim 1 wherein said plurality of biologically active entities have an anti-thrombin III binding activity of at least 9 picomoles anti-thrombin III per square centimeter (pmol/cm²) substrate material following sterilization of said biologically active entities.

23. The sterilized medical device of claim 22 wherein said plurality of biologically active entities comprises a glycosaminoglycan.

24. The sterilized medical device of claim 22 wherein said plurality of biologically active entities comprises end-point attached heparin.

25. The sterilized medical device of claim 22 wherein at least a portion of said biologically compatible organic composition is released from said sterilized medical device in a 0.15M phosphate buffer solution having a temperature of about thirty-seven degrees centigrade and a substantially neutral pH.

26. The sterilized medical device of claim 1 wherein said plurality of biologically active entities have an anti-thrombin III binding activity of at least 10 picomoles anti-thrombin III per square centimeter (pmol/cm²) substrate material following sterilization of said biologically active entities.

27. The sterilized medical device of claim 26 wherein said plurality of biologically active entities comprises a glycosaminoglycan.

28. The sterilized medical device of claim 26 wherein said plurality of biologically active entities comprises end-point attached heparin.

29. The sterilized medical device of claim 26 wherein at least a portion of said biologically compatible organic composition is released from said sterilized medical device in a 0.15M phosphate buffer solution having a temperature of about thirty-seven degrees centigrade and a substantially neutral pH.

30. The sterilized medical device of claim 1 wherein said polymeric covering material comprises multiple layers, wherein chemical components of at least one layer are cross-linked.

31. The sterilized medical device of claim 1 wherein said fluoropolymeric material is polytetrafluoroethylene.

32. The sterilized medical device of claim 1 wherein said polymeric covering material comprises at least one layer of polyethylene imine.

33. A sterilized medical device comprising:
a fluoropolymeric substrate material;
a polymeric covering material comprising imine groups that is attached to at least a portion of a surface of said substrate material;
a first plurality of heparin molecules having anti-thrombin III binding activity end point attached to at least a portion of said polymeric covering material; and
a biologically compatible organic composition non-covalently combined with said first plurality of heparin molecules,
wherein said biologically compatible organic composition comprises a carbohydrate,
wherein said first plurality of heparin molecules have an anti-thrombin III binding activity of at least 10 picomoles anti-thrombin III per square centimeter (pmol/cm$^2$) substrate material following ethylene oxide sterilization of said first plurality of heparin molecules.

34. The sterilized medical device of claim 33 wherein at least a portion of said biologically compatible organic composition is released from said sterilized medical device in a 0.15M phosphate buffer solution having a temperature of about thirty-seven degrees centigrade and a substantially neutral pH.

35. The sterilized medical device of claim 33 wherein said biologically compatible organic composition is a polysaccharide.

36. The sterilized medical device of claim 35 wherein said polysaccharide comprises a glycosaminoglycan.

37. The sterilized medical device of claim 35 wherein said polysaccharide is an anticoagulation agent.

38. The sterilized medical device of claim 37 wherein said anticoagulation agent is heparin.

39. The sterilized medical device of claim 35 wherein said polysaccharide is dextran.

40. The sterilized medical device of claim 35 wherein said polysaccharide is dextran sulfate.

41. The sterilized medical device of claim 33 wherein said polymeric covering material comprises at least one layer of polyethylene imine.

42. The sterilized medical device of claim 33 wherein said polymeric covering material comprises multiple layers, wherein chemical components of at least one layer are cross-linked.

43. The sterilized medical device of claim 33 wherein said fluoropolymeric material is polytetrafluoroethylene.

44. The sterilized medical device of claim 33 wherein said polymeric covering material comprises at least one layer of polyethylene imine.

45. A sterilized medical device comprising:
a fluoropolymeric substrate material;
a polymeric covering material comprising imine groups that is attached to at least a portion of a surface of said substrate material;
a first plurality of heparin molecules having anti-thrombin III binding activity end point attached to at least a portion of said polymeric covering material; and
a composition comprising a second plurality of heparin molecules non-covalently combined with said first plurality of heparin molecules;
wherein said first plurality of heparin molecules have an anti-thrombin III binding activity of at least 10 picomoles anti-thrombin III per square centimeter (pmol/cm$^2$) substrate material following ethylene oxide sterilization of said first plurality of heparin molecules.

46. The sterilized medical device of claim 45 wherein at least a portion of said second plurality of heparin molecules is released from said sterilized medical device in a 0.15M phosphate buffer solution having a temperature of about thirty-seven degrees centigrade and a substantially neutral pH.

47. The sterilized medical device of claim 45 wherein said polymeric covering material comprises multiple layers, wherein chemical components of at least one layer are cross-linked.

48. The sterilized medical device of claim 45 wherein said fluoropolymeric material is polytetrafluoroethylene.

49. The sterilized medical device of claim 45 wherein said polymeric covering material comprises at least one layer of polyethylene imine.

50. A sterilized medical device comprising:
a fluoropolymeric substrate material;
a polymeric covering material comprising imine groups that is attached to at least a portion of a surface of said substrate material;
a first plurality of heparin molecules having anti-thrombin III binding activity end point attached to at least a portion of said polymeric covering material; and
a composition comprising a second plurality of heparin molecules non-covalently combined with said first plurality of heparin molecules,
wherein said first plurality of heparin molecules have an anti-thrombin III binding activity of at least 100 picomoles anti-thrombin III per square centimeter (pmol/cm$^2$) substrate material following ethylene oxide sterilization of said first plurality of heparin molecules.

51. The sterilized medical device of claim 50 wherein at least a portion of said second plurality of heparin molecules is released from said sterilized medical device in a 0.15M phosphate buffer solution having a temperature of about thirty-seven degrees centigrade and a substantially neutral pH.

52. The sterilized medical device of claim 50 wherein said polymeric covering material comprises multiple layers, wherein chemical components of at least one layer are cross-linked.

53. The sterilized medical device of claim 50 wherein said fluoropolymeric material is polytetrafluoroethylene.

54. The sterilized medical device of claim 50 wherein said polymeric covering material comprises at least one layer of polyethylene imine.

* * * * *